United States Patent [19]

Yamamura et al.

[11] 4,430,265
[45] * Feb. 7, 1984

[54] GLUCOSAMINE DERIVATIVES

[75] Inventors: Yuichi Yamamura, Takarazuka; Azuma Ichiro, Suita; Shigeru Kobayashi, Hirakata, all of Japan

[73] Assignee: Takeda Chemical Industries, Ltd., Osaka, Japan

[*] Notice: The portion of the term of this patent subsequent to Jan. 18, 2000 has been disclaimed.

[21] Appl. No.: 393,870

[22] Filed: Jun. 30, 1982

Related U.S. Application Data

[63] Continuation of Ser. No. 249.902, Apr. 1, 1981, abandoned, which is a continuation of Ser. No. 962,033, Nov. 20, 1978, abandoned.

[30] Foreign Application Priority Data

Dec. 2, 1977 [JP] Japan .................. 52-145415
Dec. 2, 1977 [JP] Japan .................. 52-145416
Mar. 10, 1978 [JP] Japan .................. 53-28012

[51] Int. Cl.$^3$ .......................... C07C 103/52
[52] U.S. Cl. ............................. 260/112.5 R
[58] Field of Search ................. 260/112.5 R

[56] References Cited

U.S. PATENT DOCUMENTS 4,082,735 4/1978 Jones et al. .................. 260/112.5 R
4,082,736 4/1978 Jones et al. .................. 260/112.5 R
4,369,178 1/1983 Yamamura et al. ......... 260/112.5 R

FOREIGN PATENT DOCUMENTS 2655500 6/1977 Fed. Rep. of Germany ... 260/112.5 R
2355505 6/1976 France ......................... 260/112.5 R

OTHER PUBLICATIONS

Annals New York Academy of Sciences, vol. 277, (1976) pp. 209-227.
Gann, 69, 619-626 (1978).
Adv. Immunol. 18, 231-233 (1974).
Cancer Immunol. Immunother. 4, 95-100 (1978).
Nature New Biology 243, (1973) 216-217.
Japan J. Microbiol. 19, (4) 255-264 (1975).
Biochem. and Biophys. Res. Commun. 72, (1976) 339-346.
Gann, 67, 733-736 (1976).
Biken Journal, vol. 18, 105-111 (1975).
Gann, 67, 867-877 (1976).

*Primary Examiner*—Delbert R. Phillips
*Attorney, Agent, or Firm*—Wenderoth, Lind & Ponack

[57] ABSTRACT

Compounds of the following formula and their physiologically acceptable salts are novel and have excellent immunostimulatory activity:

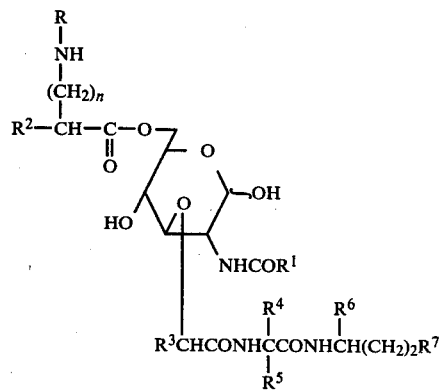

14 Claims, No Drawings

GLUCOSAMINE DERIVATIVES

This application is a continuation of application Ser. No. 249,902, filed Apr. 1, 1981, which application is a continuation of application Ser. No. 962,033, filed Nov. 20, 1978 (both now abandoned).

The present invention relates to novel and useful glucosamine derivatives.

The present inventors have succeeded in producing novel glucosamine derivatives of the formula:

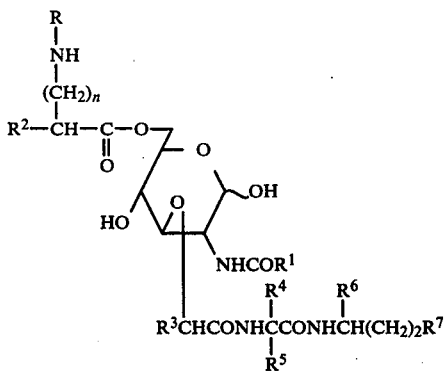

wherein
n is zero or an integer of 1 to 9;
$R^1$ is lower alkyl;
$R^2$ is hydrogen or lower alkyl when n is zero, and hydrogen or amino when n is an integer of 1 to 9;
$R^3$ is lower alkyl;
$R^4$ and $R^5$, independently of each other, are hydrogen, lower alkyl or hydroxymethyl; $R^6$ and $R^7$, independently of each other, are a carboxyl group which may be amidated;
R is hydrogen or a group of the formula R'CO—[- wherein R' is an acyclic hydrocarbon group which may be substituted by a cyclic hydrocarbon group at its ω-position] or a group of the formula

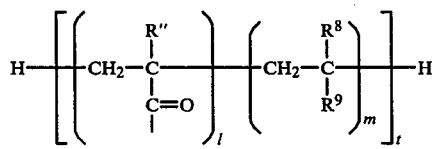

[wherein
l is an integer of 1 to 9;
m is zero or an integer of 1 to 9;
t is an integer of 2 to 100;
R" is hydrogen or lower alkyl;
$R^8$ is hydrogen or lower alkyl;
$R^9$ is lower alkyl, a carboxyl group which may be esterified, a hydroxyl group which may be etherified or a pyrrolidino group which may be substituted;
l and m are variable within the said respective ranges and $R^8$ and $R^9$ are variable within the said definition, in the respective repeating units].

Further studies on the compounds of the formula (I) have unexpectedly revealed that these compounds and salts thereof exhibit excellent immunostimulatory activity, especially cell-mediated immunostimulatory activity, and are of value, for example, as anti-infective agents, anti-mumour agents or immuno-adjuvants.

Thus, the principal object of the present invention is to provide the novel and useful compounds (I) and their salts which have excellent immunostimulatory activity, and another object is to provide a pharmaceutical composition comprising one or more of these compounds. Other objects will be made clear from the description and claims presented hereinafter.

Referring to the formula (I), the lower alkyl for $R^1$, $R^2$, $R^3$, $R^4$, $R^5$ may be either straight-chain or branched, preferably containing up to 6 carbon atoms. Thus, for example, methyl, ethyl, n-propyl, isopropyl, etc. as well as butyl, pentyl, hexyl and other groups which are straight-chain or branched at optional positions may be mentioned. Particularly desirable are lower alkyls containing up to 4 carbon atoms.

In formula (I), n is zero or an integer of 1 to 9, and $R^2$ is hydrogen or lower alkyl when n is zero, and hydrogen or amino when n is an integer of 1 to 9. The group —$(CH_2)_n$—NH— and $R^2$ may, taken together with the adjacent α-carbon atom, form a five- to eight-membered ring. Thus, as examples of such a five- to eight-membered ring, there may be mentioned pyrrolidine, imidazolidine, perhydroazepine and perhydroazocine.

Among compounds of the formula (I), those in which both $R^1$ and $R^3$ are methyl are particularly desirable. Moreover, when $R^4$ is hydrogen, $R^5$ is preferably lower alkyl or hydroxymethyl, and when $R^4$ is lower alkyl, it is preferable that $R^5$ be also lower alkyl.

Referring to the compounds (I), the $R^3$-substituted acetic acid residue attached to oxygen atom at the 3-position of the glucosamine residue has the D-configuration, and the $R^4$, $R^5$-substituted aminoacyl residue has preferably the L-configuration when both of $R^4$ and $R^5$ are not hydrogen atoms or the same lower alkyl groups at the same time while the $R^6$-substituted amino acid has desirably the D-configuration.

$R^6$ and $R^7$ in the formula (I), independently of each other, are a carboxyl group which may be amidated. Preferably, $R^6$ is carbamoyl and $R^7$ is a free carboxyl group.

In the formula (I), R is hydrogen or a group of the formula $$R'CO— \qquad (II)$$

[wherein R' is as previously defined] or a group of the formula

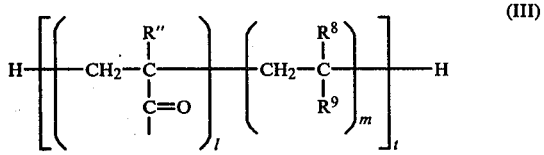

[wherein l, m, t, R", $R^8$ and $R^9$ are each as previously defined]. Thus, the formula (I) includes compounds of the formula

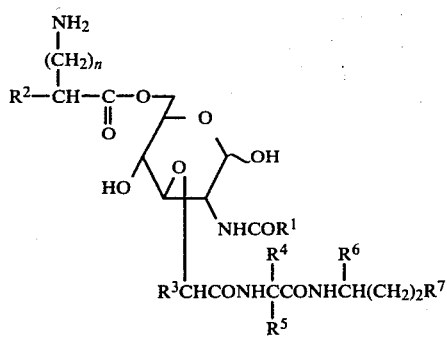

compounds of the formula

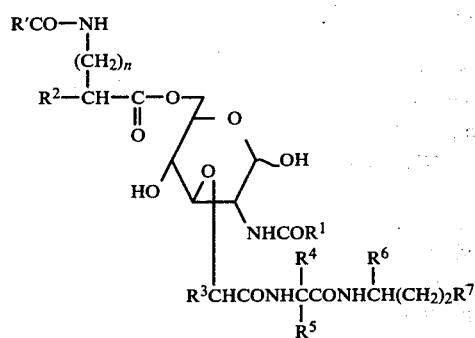

and polymers which comprise as the repeating unit or units thereof a monomeric unit of the following formula (Ic) or the same unit (Ic) and a monomeric unit of formula (IV).

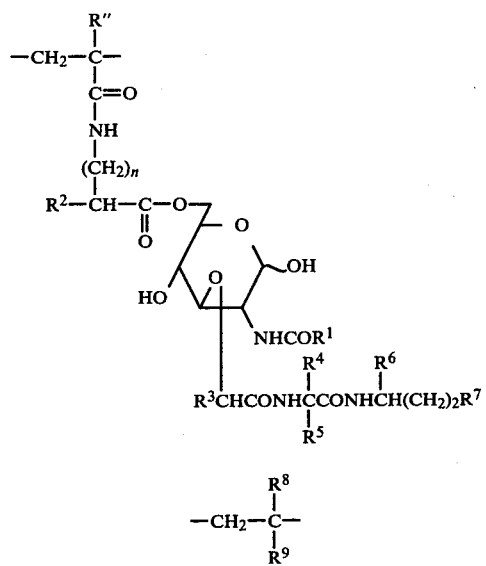

[all the symbols in the above formulas (Ia), (Ib), (Ic) and (IV) are each as previously defined].

Referring to the formulas (Ib) and (II), R' is an acyclic hydrocarbon group which may be substituted by a cyclic hydrocarbon group at its ω-position. This acyclic hydrocarbon group may be straight-chain or branched, and saturated or unsaturated. In the case of an unsaturated acyclic hydrocarbon group involving multiple bonding, those bonds may be either independent or conjugated. When a double bond is involved, the main chain may be optionally trans or cis-oriented with respect to the double bond. Generally speaking, acyclic hydrocarbon groups containing up to 41 carbon atoms are preferred. As examples of such acyclic hydrocarbon groups, there may be mentioned, as represented by the formula R'CO—, acetyl, acryloyl, propionyl, methacryloyl, butyroyl, valeroyl, nonanoyl, trans-13-docosenoyl, palmitoyl, stearoyl, oleoyl, geranylacetyl, digeranylacetyl, farnesylacetyl, geranylgeranylacetyl, di(geranylgeranyl)acetyl, etc. The cyclic hydrocarbon group which may optionally be present as the ω-substituent of such an acyclic hydrocarbon group is preferably a six-membered unsaturated hydrocarbon group such as phenyl, cyclohexenyl and cyclohexadienyl. Such a cyclic hydrocarbon group may have 1 to 3 or more substituents at optional positions of its ring, such as lower alkyl (e.g. methyl, ethyl, isopropyl, etc.; preferably of up to 3 carbon atoms), lower alkoxy (e.g. methoxy, ethoxy, propoxy, etc.; preferably of up to 3 carbon atoms) and/or oxo, for instance. The most desirable is 2,3-dimethoxy-5-methyl-1,4-benzoquinone-6-yl. As examples of acyclic hydrocarbon groups substituted by such cyclic hydrocarbon groups at the ω-position, there may be mentioned, as represented by the formula R'CO—, 3-(2,3-dimethoxy-5-methyl-1,4-benzoquinon-6-yl)-propionyl; 6-(2,3-dimethoxy-5-methyl-1,4-benzoquinon-6-yl)-hexanoyl; 10-(2,3-dimethoxy-5-methyl-1,4-benzoquinon-6-yl)-decanoyl; retinoyl; 6-(3,4,5-trimethyl-1,4-benzoquinon-6-yl)-4-methyl-4-hexenoyl; 6-(3,4-dimethoxy-5-methyl-1,4-benzoquinon-6-yl)-4-methyl-4-hexenoyl; 6-(2-methyl-1,4-naphthoquinon-3-yl)-4-methyl-4-hexenoyl; 4-(3,4,5-trimethyl-1,4-benzoquinon-6-yl)-2-methyl-butyroyl; 4-(3,4-dimethoxy-5-methyl-1,4-benzoquinon-6-yl)-2-methyl-butyroyl; 4-(2-methyl-1,4-naphthoquinon-3-yl)-2-methyl-butyroyl; 6-(2,3,5-trimethyl-1,4-benzoquinon-6-yl)hexanoyl; 5-(2-methyl-1,4-naphthoquinon-3-yl)-pentanoyl; 3-{-[3,4-dihydro-2,5,7,8-tetramethyl-2-(4,8,12 -trimethyl-tridecyl)-2H-1-benzopyran-6-yl]oxycarbonyl}-propanoyl; and so forth. Among the acyclic hydrocarbon groups described above, the acyclic hydrocarbon groups of 11 to 41 carbon atoms which are not substituted by cyclic hydrocarbon groups at ω-positions and the acyclic hydrocarbon groups of 2 to 9 carbon atoms which are substituted by said cyclic hydrocarbon groups at ω-positions are preferred.

Referring to the formulas (Ic), (III) and (IV), lower alkyl for R", $R^8$ or $R^9$ may be straight-chain or branched and preferably of up to 4 carbon atoms. As examples thereof, there may be mentioned methyl, ethyl, n-propyl, isopropyl, and n-butyl. In these formulas, $R^9$ is lower alkyl, a carboxyl group which may be esterified, a hydroxyl group which may be etherified or a pyrrolidino group which may be substituted. As typical examples of such an esterified carboxyl group there may be mentioned the carboxyl groups esterified by alkanols. As examples of said alkanols there may be mentioned methanol, ethanol, propanol, 2,2-dimethyl-1-propanol, butanol, 3-methyl-2-butanol, 2-ethyl-1-butanol, pentanol, isopentanol, 2-methyl-1-pentanol, 3-ethyl-3-pentanol, 2,2,4-trimethyl-1-pentanol, hexanol, 2-ethyl-1-hexanol, heptanol, 2,6-dimethyl-4-heptanol, octanol, 2-methyl-3-octanol, nonanol, decanol, undecanol, 7-ethyl-2-methyl-4-undecanol, dodecanol, tridecanol, tetradecanol, pentadecanol, hexadecanol, heptadecanol, octadecanol, nonadecanol, eicosanol, heneicosanol, tricosanol, tetracosanol, hexacosanol, etc. Particularly preferred are higher alkanols containing about 10 to 22 carbon atoms. The etherified hydroxyl groups are desirably hydroxyls etherified by alkyls which may for example be methyl, ethyl, propyl, 2-methylpropyl, butyl, 2-methylbutyl, 3-methylbutyl, pentyl, hexyl, 2-ethylhexyl, heptyl, octyl, nonyl, decyl, undecyl, dodecyl, tridecyl, tetradecyl, pentadecyl, heptadecyl, octadecyl, eicosyl, docosyl, etc. Particularly preferred are higher alkyls containing about 10 to 22 carbon atoms. The pyrrolidino group $R^9$ may be substituted, the most desirable substituent group being oxo. Such a group, as $R^9$, may have such substituents as, for example, halogens (chlorine, bromine, etc.), lower alkyls (methyl, ethyl, propyl, etc.), lower alkoxy groups (methoxy, ethoxy, propoxy, etc.), nitro, amino and cyano, as will be further explained hereinafter in connection with the starting compound (IV').

With regard to the polymers according to this invention, those consisting solely of the above first unit (Ic) as the repeating unit are homopolymers, while the polymers consisting of the two monomeric units (Ic) and (IV) as repeating units thereof are copolymers. The homopolymers may be isotactic, syndiotactic or atactic. The copolymers may be regular, block or random copolymers. These homopolymers and copolymers may not only be head-to-tail polymers but be of irregular configurations, i.e. head-to-head or tail-to-tail. Generally speaking, the polymers according to this invention desirably have molecular weights within the range of about 1,000 to about 100,000 and, for still better results, within the range of about 1,000 to about 15,000. The most desirable range is about 1,500 to about 5,000. The molecular weights referred to in this specification are the average molecular weights as determined by the vapor pressure osmometry [Miller and Stolten; Anal. Chem. 25(1953), 1103 et seq.] for the range of about 1,000 to 15,000 and by gel-permeation chromatography [Journal of Biological Chemistry 244(1969), 4989–4994] for the range over about 15,000.

The compounds (I) of the present invention may be produced, for example, by the following Processeses A, B or/and C.

Process A

Among the compounds (I), compounds of the formula (Ia) may be produced by condensing a compound of the formula

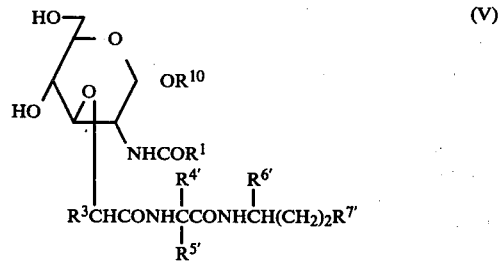

[wherein $R^{10}$ is hydrogen or a protective group; $R^1$ and $R^3$ are each as previously defined; $R^{4'}$, $R^{5'}$, $R^{6'}$ and $R^{7'}$ are respectively the same groups as those previously mentioned for $R^4$, $R^5$, $R^6$ and $R^7$ or the corresponding groups, the hydroxyl or carboxyl functions, if any, of which has been protected] with a compound of the formula

[wherein n and $R^2$ are each as previously defined; Y is an amino-protecting group] and removing the protective group or groups.

Referring to the formula (VI), the amino-protecting group Y may be any of the easily removable amino-protecting groups known per se in the field of peptide chemistry. For example, benzyloxycarbonyl (carbobenzoxy), p-methoxybenzylcarbonyl, p-methylbenzylcarbonyl, tert.-butyloxycarbonyl, tert.-amyloxycarbonyl, p-biphenylisopropyloxycarbonyl, O-nitrophenylsulfenyl and trityl may be desirably employed.

Referring to the formula (V), the protective groups which may be included in $R^{4'}$, $R^{5'}$, $R^{6'}$, $R^{7'}$ and $R^{10}$ may each be any of the easily removable groups which are known per se in the field of peptide chemistry and carbohydrate chemistry. For the protection of carboxyl, there may be mentioned tert.-butyl, benzyl and benzhydryl, in particular. As hydroxyl-protecting groups, there may be mentioned acyl groups such as lower alkanoyls (e.g. acetyl), alkyl groups (e.g., methyl and tert.-butyl), for instance. Particularly beneficial are benzyl group optionally substituted by halogen, nitro, lower alkyl or lower alkoxy.

The condensation of said compounds (V) and (VI) can be accomplished by a condensation reaction process known per se.

For example, the carboxyl group of compound (VI) is first activated and, then, the activated compound is reacted with compound (V).

As examples of such activated carboxyl groups there may be mentioned active esters and acid anhydrides.

As examples of the active esters just mentioned there may be mentioned cyanomethyl ester, thioglycolic acid ester, p-nitrophenyl ester, 2,4,5-trichlorophenyl ester, pentachlorophenyl ester, pentafluorophenyl ester, pivalohydroxanic acid ester, N-hydroxyphthalimide ester, N-hydroxysuccinimide ester, N-hydroxy-5-norbornene-2,3-dicarboximide ester, 8-hydroxyquinoline ester, 2-hydroxy-1,2-dihydro-1-carbethoxy-quinoline ester, 2-hydroxyphenyl ester, 2-hydroxy-4,5-dichlorophenyl ester, 2-hydroxypyridine ester, 2-pyridylthio ester, esters with 1-hydroxybenzotriazol which may be either unsubstituted or substituted by halogenomethyl or methoxy, and enol esters which may be obtainable with N-ethyl-5-phenyl-isooxazolium-3-sulfonate, for instance. In certain cases, said activated carboxyl groups may also be obtained in situ by adding N-hydroxysuccinimide, N-hydroxy-5-norbornene-2,3-dicarboximide, unsubstituted or halogenomethyl- or methoxy-substituted 1-hydroxybenzotriazole, 3-hydroxy-4-oxo-3,4-dihydrobenzo[d]-1,2,3-triazine or the like in the presence of N,N'-dicyclohexylcarbodiimide.

The acid anhydride is preferably a mixed acid anhydride or an acid amide, e.g. imidazolide, isooxazolide or the like, for instance.

If necessary, the reaction involving such an activated ester may be conducted in the presence of an organic base such as triethylamine, N-methylmorpholine, N-ethylmorpholine or 1-hydroxybenzotriazole.

The reaction temperature normally ranges from about 0° C. to about 80° C., the preferred range being about 5° to 50° C., although the reaction may be conducted at temperatures outside of the above range, if desired.

The reaction generally proceeds in a solvent. As examples of the solvent there may be mentioned halogenated hydrocarbons such as chloroform, carbon tetrachloride, etc.; ethers such as diethyl ether, tetrahydrofuran, dioxane, etc.; esters such as ethyl acetate, isoamyl acetate, etc.; hydrocarbons such as benzene, toluene, xylene, etc.; nitriles such as acetonitrile; N-alkylamides such as N,N-dimethylformamide, N-methyl-2-pyrrolidone, dimethylacetamide etc.; dimethylsulfoxide; hexamethylphosphoramide; and other suitable solvents.

While said compounds (V) and (VI) react stoichiometrically, it is of course not essential that these two reactants be initially present in equimolar proportions in the reaction system. Rather, with respect to compound (V), it is normally desirable to employ about 1 to 5 molar equivalents, preferably about 2 to 3 equivalents, of compound (VI). The proportions of the two reactants may be optionally selected so as to give satisfactory results, with reference to the combination of the reactants and other conditions.

Following this reaction, the protective groups may be removed by procedures known per se. Thus, for example, these groups can be removed by hydrogenolysis in the presence of a noble metal catalyst (e.g. platinum or palladium) or by acid hydrolysis.

The compounds (Ia) thus produced can be isolated, either in the free form or as one of the salts mentioned hereinafter, by treatments known per se (e.g. extraction, phase transfer, chromatography, crystallization, recrystallization, reprecipitation, etc.)

Process B

The compounds of the formula (Ib) may be produced by condensing a compound of the formula

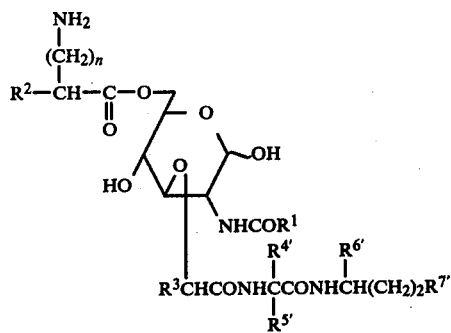

(Ia')

[wherein $R^1$, $R^2$, $R^3$, $R^{4'}$, $R^{5'}$, $R^{6'}$ and $R^{7'}$ are each as previously defined] with a compound of the formula

R'COOH (VII)

[wherein R' is as previously defined] and, if necessary, removing the protective group or groups.

The condensation reaction between compound (Ia') and compound (VII) may be carried out in the same manner as the above-mentioned condensation reaction between compound (V) and compound (VI), and the removal of protective groups and the isolation of the product (Ib) after the reaction may also be accomplished in a manner similar to that described hereinbefore.

Among the compound (Ib) thus obtained, those compounds wherein R' is a group of the formula

[wherein R'' is as previously defined] may be employed also as the intermediates in Process C mentioned below.

Process C

The polymers according to this invention can be produced by polymerizing a compound of the formula

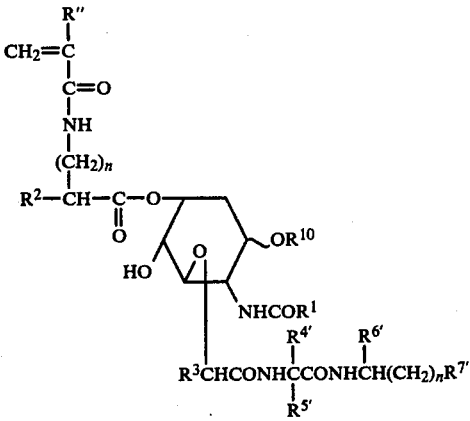

(Ic')

[wherein all the symbols are each as previously defined] either alone or together with a compound of the formula

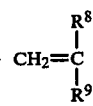

(IV')

[wherein $R^8$ and $R^9$ are as previously defined] and, if necessary, removing one or more protective groups present.

As the compound represented by general (IV') above, use may be made of the known compounds such as vinyl acetate and other vinyl esters, e.g. vinyl trifluoroacetate, vinyl propionate, vinyl caproate, vinyl stearate, etc.; methacrylic acid and methacrylic acid esters, e.g. methyl methacrylate, ethyl methacrylate, n-propyl methacrylate, iso-propyl methacrylate, n-butyl methacrylate; and acrylic acid and acrylic acid esters, e.g. methyl acrylate, ethyl acrylate, etc.; vinyl ethers, e.g. methyl vinyl ether, ethyl vinyl ether, propyl vinyl ether, n-butyl vinyl ether, isobutyl vinyl ether, β-chloroethyl vinyl ether, N-vinyl-2-pyrrolidone, N-methacryl-2-pyrrolidone, etc.

This polymerization reaction may be carried out by polymerization processes known per se. By way of example, the compound (Ic') is polymerized either alone or together with the compound (IV') in the presence of a solvent or without a solvent and in the presence of a polymerization initiator. As examples of said solvent there may be mentioned halogenated hydrocarbons (e.g. methylene chloride), ethers (e.g. tetrahydrofuran, dioxane, etc.), esters (e.g. methyl acetate, ethyl acetate, isoamyl acetate, etc.), organic acids (e.g. acetic acid, propionic acid, etc.), alcohols (e.g. methanol, ethanol, propanol, etc.), amides (e.g. dimethylformamide, etc.), sulfoxides (e.g. dimethylsulfoxide, etc.) and water.

As examples of said polymerization initiator there may be mentioned peroxides (e.g. benzoyl peroxide and substitution products thereof, tert.-butyl hydroperoxide, di-tert.-butyl peroxide), potassium persultate, ammonium persulfate, cumene-hydroperoxide, peroxides with transition metals or amines, azo compounds such as azobisisobutyronitrile, azobiscyclohexanecarbonitrile, 2,2'-azobis(2-amidinopropane) hydrochloride, 2,2'-azobis (2,4-dimethylvaleronitrile), 4,4'-azobis(4-cyano-1-pentanol) or 4,4'-azobis(4-cyanopentanoic acid), organometallic compounds such as n-butyllithium, inorganic salts such as aluminum chloride, stannic chloride, titanium tetrachloride, naphthalene sodium, boron trifluoride, diethyl ethoxide, and acids such as phosphoric acid, perchloric acid, etc.

The reaction temperature ranges normally from about room temperature (about 10°-30° C.) to about 300° C. and preferably from about 30° to 180° C. If desired, the reaction may be conducted at temperatures outside of the above range.

The reaction pressure may normally range from atmospheric pressure to about 700 kg/cm². In many cases, the reaction may be more smoothly carried out in an atmosphere of nitrogen gas.

When the compound (Ic') alone is polymerized in the above manner, there is obtained a homopolymer consisting solely of (Ic) as the repeating unit, while the polymerization of compound (Ic') together with compound (IV') yields a copolymer consisting of (Ic) and (IV) as repeating units. The ratio of repeating unit (Ic) to repeating unit (IV) in this copolymer can be controlled by varying the charge ratio of compound (Ic')/compound (IV'), among other variables.

The molecular weight of the polymer according to this invention is optional between the low and high molecular weight limits mentioned hereinbefore, although it preferably lies within the range of about 1,000 to about 15,000 and, for still better results, within the range of about 1,500 to about 5,000. Therefore, it desired, by means of a chain transfer agent for the purpose of controlling the degree of polymerization, with consideration given to the polymerization reaction solvent used from the diffusion rate point of view, a polymer having an optional molecular weight can be produced by way of the so-called telomerization. As preferred examples of said chain transfer agent there may be mentioned ethylbenzene, isopropylbenzene, triphenylmethane, chloroform, carbon tetrachloride, carbon tetrabromide, triethylamine, thiophene, etc.

The removal of protective groups and the isolation of the product after the reaction may be conducted in a manner similar to that described hereinbefore.

The compunds (I) can be isolated in the form of physiologically acceptable salts. Thus, the compounds (Ia) may be acidic, neutral or basic according to the types of substituents thereon. The compounds (Ib) and the polymers containing the repeating unit (Ic) may be acidic or neutral depending upon the types of substituents thereon. When the compound (I) are acidic, they form salts with bases. As examples of the salts with bases there may be mentioned ammonium salts and alkali metal or alkaline earth metal salts, e.g. salts with sodium, potassium, calcium and magnesium. When the compounds are basic, they are able to form acid addition salts such as salts with inorganic acids (hydrochloric acid, hydrobromic acid, phosphoric acid, nitric acid, sulfuric acid, etc.) organic carboxylic acids (e.g. acetic acid, propionic acid, maleic acid, succinic acid, malic acid, citric acid, tartaric acid, salicyclic acid, nicotinic acid, etc.) or organic sulfonic acids (e.g. methanesulfonic acid, p-toluenesulfonic acid, etc.). The compounds (I) can be employed as those physiologically acceptable salts.

The compounds (I) of the present invention have low toxicity and desirable immunostimulatory activity. Particularly, the compounds (I) significantly enhance the cell-mediated immunity which play a major role for the anti-infection and suppressive effect on cancer. This fact can be established by the following experiments.

The ability of the compound (I) to stimulate the cell-mediated immunity of recipient hosts can be established by their immunoenhancing effect on the induction of delayed type hypersensitivity to N-acetyltyrosine-3-azobenzene-4'-arsonic acid (ABA-N-Ac-Tyr) in guinea pigs. Thus, a mixed solution of ABA-N-Ac-Tyr (50 μg per animal) and the compound (I) of this invention (10-200 μg per animal) in phosphate buffered saline was admixed with Freund's incomplete adjuvant to prepare a water-in-oil emulsion and guinea pigs (Hartley strain) were immunized by injecting the emulsion into the footpad of each animal in a dose of 0.05 ml. After 2 weeks the back of each animal was shaved and ABA-bacterial α-amylase [ABA-BαA] (100 μg) was intraperitoneally administered. After 24 and 48 hours, the diameters of skin reactions (erythema and induration) were measured. These diameters serve as a measure of cell-mediated immunity. The results with regard to the representatives of the compounds (I) are summarized in Table 1 below.

As a control, when a solution of ABA-N-Ac-Tyr, which is the antigen, alone in phosphate buffered saline was admixed with Freund's incomplete adjuvant to prepare a water-in-oil emulsion and this emulsion was similarly administered, there was induced no delayed type hypersensitivity to ABA-N-Ac-Tyr.

TABLE 1

| Compound | Dose (μg) | Skin reaction to ABA-BαA(mm ± S.E.*) 24 hr. | 48 hr. |
|---|---|---|---|
| 2-{2-Acetamido-2-deoxy-6-O—glysyl-D-glucos-3-O-yl)-D-propionyl-L-alanyl-D-isoglutamine | 100 | 17.0 ± 0.6 | 13.7 ± 0.7 |
| Homopolymer of 2-[2-acetamido-2-deoxy-6-O—(methacryloyl-β-alanyl)-D-glucos-3-O—yl]-D-propionyl-L-alanyl-D-isoglutamine (MW Ca.2000) | 10 100 | 18.8 ± 0.5 20.3 ± 0.8 | 18.1 ± 0.1 19.8 ± 0.7 |
| 2-{2-Acetamido-2-deoxy-6-O—[3-(2,3-dimethoxy-5-methyl-1,4-benzoquinon-6-yl)-propionyl-11-aminoundecanoyl]-D-glucos-3-O—yl}-D-propionyl-L-alanyl-D-isoglutamine | 200 | 20.0 ± 0.5 | 22.3 ± 1.2 |
| 2-{2-Acetamido-2-deoxy-6-O—[10-(2,3-dimethoxy-5-methyl-1,4-benzoquinon-6-yl)-decanoyl-L-leucyl]-D-glucos-3-O—yl}-D-propionyl-α-aminoisobutyroyl-D-isoglutamine | 200 | 22.0 ± 1.0 | 24.0 ± 1.7 |
| Control | — | 0 | 0 |

*S.E.: Standard error

The cell-mediated immunostimlatory activity of the compounds (I) is also evident from the fact that they are able to markedly amplify the onset of cytotoxicity. [The induction of lymphocytes specifically toxic to target cells (cancer cells)]. Thus, C57BL/6J mice (H-2$^b$) are intraperitoneally injected with Mastocytoma P815-

X2(H-2$^d$) cells, with or without one of the compounds according to this invention as dissolved in phosphate-buffered saline. On day-11 after this immunization, the spleen of each mouse is enucleated and the T-cell (Killer-T cell) population cytotoxic to the target cells produced in the spleen is determined by the method of Brunner (Immunology 18, 501–515). The concurrent administration of a compounds (I) and said Mastocytoma cells resulted in a marked increase in the Killer-T cell population in the spleen. While a cancer therapy designed to reject cancer cells, which are non-autologous cells, by increasing the immunological responsiveness of the patient has been widely practiced in recent years, it is thought to be the Killer-T cell that plays a major role in this therapy. In this sense, the Killer-T population as stimulated by the administration of the compounds (I) may be regarded as a measure of antitumour activity.

By virtue of the aforementioned properties, the compounds (I) according to this invention can be employed for the treatment of many diseases attributable to cell-mediated immunity depressions, for example as anti-infective agents.

On the one hand, because the compound (I) are capable of stimulating the immunogenicity of an antigen when used in combination therewith, they are suitable for use in admixture with various antigens in the production of diagnostic and therapeutic antisera. Moreover, the compounds(I) can be employed for the purpose of potentiating the immunity already latent in the body, without concomitant addition of antigens. Therefore, the compounds (I) are particularly effective in cases of chronic and acute infectious diseases, in cases of general immunological incompetence, innate or acquired, e.g. those encountered in the course of a serious primary disease at an advanced age. The compounds (I) can thus be administered to warm-blooded animals (e.g. man; laboratory animals such as mouse, guinea pig, rat, etc.; pet animals such as dog, cat, etc.) either enterally, e.g. orally or rectally, or parenterally. The dosage depends on the individual conditions of the animal, its species and age and the dosage form used. When,/ for example, the compound is used as an injectable isotonic solution, e.g. an isotonic aqueous solution such as a salt-containing solution or a glucose solution, for subcutaneous, intracutaneous or intramuscular administration, the preferred dosage may range from about 1 to 500 μg/kg/day (as the anhydrate of the compound) and, particularly, from about 5 to 30 μg/kg/day (on the same basis.)

For such parenteral administration, the compound may also be administered in the form of a stabilized water-in-oil emulsion, the oil being preferably of the vegetable or animal origin. Such a vegetable or animal oil emulsion may comprise about 5 to 100 volume parts of the isotonic aqueous solution and one volume part of a metabolizable vegetable or animal oil, supplemented with an emulsion stabilizer, for instance.

For administration by the oral route, the compound may be formulated with a pharmaceutically acceptable excipient and used as sugar-coated tablets, capsules, etc., the dosage in such forms being between about 40 and 4000 μg/kg/day.

The compounds (I) of this invention are advantageous in that, in addition to the above-mentioned desirable biological activity, the compounds are water-soluble in contrast to the sparingly soluble nature of the 6-O-acylglucosamine derivatives which have been heretofore reported to have antitumour activity.

The starting compound (V) according to the present invention can be easily prepared, for example by the process described in Biochemical and Biophysical Research Communications 66, 1316–1322(1975) or any process analogous thereto, and the compound (VI) can be easily prepared by the process described in Greenstein & Winitz: Chemistry of the Amino Acids, 887–901, John Wiley and Sons, Inc. (1961) or any process analogous thereto.

The following Examples are intended merely to illustrate presently preferred embodiments of the present invention and not to restrict the scope of this invention.

EXAMPLE 1

(1) In N,N-dimethylformamide (15 ml) was dissolved benzyl 2-(benzyl 2-acetamido-2-deoxy-α-D-glucopyranosid-3-O-yl)-D-propionyl-L-alanyl-D-isoglutaminate (1.35 g, 2 m mols), followed by addition of carbobenzoxy-glycine p-nitrophenyl ester (1.32 g, 4 m mols), 1-hydroxybenzotriazole (1.08 g, 8 m mols) and N-ethylmorpholine (1.02 ml, 8 m mols). The mixture was stirred at room temperature for 3 days, after which time the solvent was distilled off under reduced pressure. The residue was dissolved in ethyl acetate, and the solution was washed with 5% aqueous sodium hydrogen carbonate, 0.2 N-hydrochloric acid and water in the order mentioned and dried over anhydrous sodium sulfate. The solvent was distilled off and the residue was purified by precipitation from a solvent mixture of ethyl acetatediethyl ether-petroleum ether, which provided a gel. By the above procedure there was obtained 1.13 g of benzyl 2-[benzyl 2-acetamido-6-O-(carbobenzoxyglycyl)-2-deoxy-α-D-glucopyranosid-3-O-yl]-D-propionyl-L-alanyl-D-isoglutaminate. m.p. 192°–193° C.; $[\alpha]_D^{23}+80.2°$ (c=0.5, N-dimethylacetamide): Rf=0.47 (chloroform-methanol-acetic acid=18:2:1; silica gel plate)(The Rf values found under the above conditions will all be designated by the symbol Rf$^1$.)

Elemental analysis, for $C_{43}H_{53}O_{14}N_5$; Calcd. C, 59.78; H, 6.18; N, 8.11; Found C, 59.65; H, 6.01; N, 7.96.

(2) In acetic acid (12 ml) was dissolved benzyl 2-[benzyl 2-acetamido-6-O-(carbobenzoxyglycyl)-2-deoxy-α-D-glucopyranosid-3-O-yl]-D-propionyl-L-alanyl-D-isoglutaminate (864 mg, 1 m mol) and, with palladium black as a catalyst, hydrogenation was carried out at room temperature and atmospheric pressure until the reaction had ceased to proceed. The catalyst was separated by filtration and washed with a small amount of water. The filtrate was concentrated to dryness and the residue was applied to a column of Sephadex LH-20, elution being carried out with ethanol-0.1 N acetic acid (3:2). By the above procedure there was obtained 464 mg of 2-(2-acetamido-2-deoxy-6-O-glycyl-D-glucos-3-O-yl)-D-propionyl-L-alanyl-D-isoglutamine (hereinafter, this compound will be designated as 6-O-glycyl-N-acetylmuramyl-L-alanyl-D-isoglutamine) m.p. 104°–107° C. $[\alpha]_D^{23}+48.0°$ (c=0.5, N,N-dimethylformamide); Rf=0.32 (n-butanol-ethyl acetate-acetic acid-water=1:1:1:1; silica gel plate) (The Rf values found under the above conditions will all be designated by the symbol Rf$^2$).

Elemental analysis, for $C_{21}H_{35}O_{12}N_5 \cdot \frac{1}{2}H_2O$; Calcd. C, 45.16; H, 6.50; N, 12.54; Found C, 45.55; H, 6.65; N, 12.49.

EXAMPLE 2

(1) In N,N-dimethylformamide (30 ml) was dissolved benzyl 2-(benzyl-2-acetamido-2-deoxy-α-D-glucopyranosid-3-O-yl)-D-propionyl-L-alanyl-D-isoglutaminate (7.74 g, 11.5 m mols), followed by addition of carbobenzoxy-β-alanine p-nitrophenyl ester (10.33 g, 30 m mols), 1-hydroxybenzotriazole (3.11 g, 23 m mols) and N-ethylmorpholine (2.94 ml, 23 m mols). The mixture was stirred at room temperature for 2 days, after which the solvent was distilled off under reduced pressure. The residue was dissolved in ethyl acetate, washed with 5% aqueous sodium hydrogen carbonate, 1 N-hydrochloric acid and saturated aqueous sodium chloride in the order mentioned and dried over anhydrous sodium sulfate. The solvent was distilled off and the residue was purified by column chromatography on silica gel, elution being carried out with chloroform-acetone-methanol (10:3:2). By the above procedure there was obtained 7.12 g of benzyl 2-[benzyl 2-acetamido-6-O-(carbobenzoxy-β-alanyl)-2-deoxy-α-D-glucopyranosid-3-O-yl]-D-propionyl-L-alanyl-D-isoglutaminate as powders melting at 152°–154° C.; $[\alpha]_D^{23} + 77.5°$ (c=0.5, N,N-dimethylformamide); $Rf^1 = 0.48$.

Elemental analysis, for $C_{44}H_{55}O_{14}N_5$; Calcd. C, 60.19; H, 6.31; N, 7.98; Found C, 59.79; H, 6.31; N, 7.82.

(2) In the same manner as Example 1-(2), benzyl 2-[benzyl 2-acetmaido-6-O-(carbobenzoxy-β-alanyl)-2-deoxy-α-D-glucopyranosid-3-O-yl]-D-propionyl-L-alanyl-D-isoglutaminate (4.39 g, 5 m mols) was hydrogenated in acetic acid and in the presence of palladium black and the reaction product was purified. By the above procedure there was obtained 2-(2-acetamido-6-O-β-alanyl-2-deoxy-D-glucos-3-O-yl)-D-propionyl-L-alanyl-D-isoglutamine (hereinafter referred to as 6-O-β-alanyl-N-acetylmuramyl-L-alanyl-D-isoglutamine) in quantitative yield. m.p. 87°–91° C. (decomp.); $[\alpha]_D^{23} + 33.2°$ (c=0.5, N,N-dimethylformamide); $Rf^2 = 0.32$ Elemental analysis, for $C_{22}H_{37}O_{12}N_5 \cdot \frac{1}{2}H_2O$; Calcd. C, 46.15; H, 6.69; N, 12.23; Found C, 46.46; H, 6.99; N, 11.95.

EXAMPLE 3

(1) In N,N-dimethylformamide (30 ml) was dissolved benzyl 2-(benzyl 2-acetamido-2-deoxy-α-D-glucopyranosid-3-O-yl)-D-propionyl-L-alanyl-D-isoglutaminate (3.36 g, 5 m mols), followed by addition of carbobenzoxy-ε-amino-n-caproic acid p-nitrohenyl ester (3.86 g, 10 m mols) and 1-hydroxybenzotriazole (2.70 g, 20 m mols). After 2.6 ml of triethylamine was added under ice-cooling, the mixture was stirred at room temperature for 16 hours. The precipitate was removed and the solvent was distilled off under reduced pressure. The residue was dissolved in ethyl acetate, washed with 5% aqueous sodium hydrogen carbonate, 0.5 N-hydrochloric acid and water in the order mentioned and dried over anhydrous sodium sulfate. The solvent was distilled off and the residue was purified by silica gel column chromatography, elution being carried out with chloroform-acetone-methanol (10:3:1). The product was reprecipitated from ethyl acetate-diethyl ether. By the above procedure there was obtained 1.27 g of benzyl 2-[benzyl 2-acetamido-6-O-(carbobenzoxy-ε-amino-n-caproyl)-2-deoxy-α-D-glucopyranosid-3-O-yl]-D-propionyl-L-alanyl-D-isoglutaminate. m.p. 161°–162° C.; $[\alpha]_D^{23} + 74.8°$ (c=0.5, N,N-dimethylformamide); $Rf^1 = 0.54$ Elemental analysis, for $C_{47}H_{61}O_{14}N_5$; Calcd. C, 61.36; H, 6.68; N, 7.61; Found C, 61.49; H, 6.69; N, 7.37.

(2) In the same manner as Example 1-(2), benzyl 2-[benzyl-2-acetamido-6-O-(carbobenzoxy-ε-amino-n-caproyl)-2-deoxy-α-D-glucopyranosid-3-O-yl]-D-propionyl-L-alanyl-D-isoglutaminate (374 mg, 0.4 m mol) was hydrogenated in acetic acid and in the presence of palladium black, and the reaction product was purified. By the above procedure there was obtained 202 mg of 2-[2-acetamido-6-O-(ε-amino-n-caproyl)-2-deoxy-D-glucos-3-O-yl]-D-propionyl-L-alanyl-D-isoglutamine (hereinafter referred to as 6-O-ε-amino-n-caproyl-N-acetylmuramyl-L-alanyl-D-isoglutamine.) m.p. 96°–97° C.; $[\alpha]_D^{23} + 24.0°$ (c=0.5, N,N-dimethylformamide); $Rf^2 = 0.40$ Elemental analysis, for $C_{25}H_{43}O_{12}N_5 \cdot 3/2H_2O$; Calcd. C, 47.46; H, 7.33; N, 11.07; Found C, 47.50; H, 7.34; N, 10.57.

EXAMPLE 4

(1) In the same manner as Example 1-(1), carbobenzoxy-L-proline p-nitrophenyl ester (1.48 g, 4 m mols) and benzyl 2-(benzyl 2-acetamido-2-deoxy-α-D-glucopyranosid-3-O-yl)-D-propionyl-L-alanyl-D-isoglutaminate (1.34 g, 2 m mols) were reacted in N,N-dimethylformamide (10 ml) and in the presence of 1-hydroxybenzotriazole (1.08 g, 8 m mols) and N-ethylmorpholine (1.02 ml, 8 m mols) and the reaction product was purified. By the above procedure there was obtained 732 mg of benzyl 2-(benzyl-2-acetamido-6-O-(carbobenzoxy-L-prolyl)-2-deoxy-α-D-glucopyranosid-3-O-yl]-D-propionyl-L-alanyl-D-isoglutaminate. m.p. 110°–112° C.; $[\alpha]_D^{23} + 61.1°$ (c=0.5, N,N-dimethylformamide); $Rf^1 = 0.57$ Elemental analysis, for $C_{46}H_{57}O_{14}N_5$; Calcd. C, 61.11; H, 6.36; N, 7.75; Found C, 61.15; H, 6.45; N, 7.53.

(2) In the same manner as Example 1-(2), benzyl 2-[benzyl 2-acetamido-6-O-(carbobenzoxy-L-prolyl)-2-deoxy-α-D-glucopyranosid-3-O-yl]-D-propionyl-L-alanyl-D-isoglutaminate (482 mg, 0.53 m mol) was hydrogenated in acetic acid and in the presence of palladium black, and the reaction product was purified. By the above procedure there was obtained 2-(2-acetamido-2-deoxy-6-O-L-prolyl-D-glucos-3-O-yl)-D-propionyl-L-alanyl-D-isoglutamine in quantitative yield. m.p. 159° C. (decomp.); $[\alpha]_D^{23} + 37.6°$ (c=0.5, N,N-dimethylformamide); $Rf^2 = 0.29$.

Elemental analysis, for $C_{24}H_{39}O_{12}N_5 \cdot 1.5H_2O$; Calcd. C, 46.75; H, 6.87; N, 11.35; Found C, 47.06; H, 7.00; N, 10.77.

EXAMPLE 5

(1) N-t-butyloxycarbonyl-O-benzyl-L-serine (4.43 g, 15 m mols) and D-isoglutamine benzyl ester (3.54 g, 15 m mols) were dissolved in acetonitrile (100 ml), and under ice-cooling, N,N'-dicyclohexylcarbodiimide (3.50 g, 17 m mols) was added. The mixture was stirred under ice-cooling for 3 hours and, then, at room temperature for 15 hours. The precipitate was filtered off, the solvent was distilled off and the residue was dissolved in ethyl acetate (100 ml). The solution was washed with 1 N-hydrochloric acid, 5% aqueous sodium hydrogen carbonate and water in the order mentioned and dried over anhydrous sodium sulfate. The solvent was distilled off and the residue was crystallized from ethyl acetate-petroleum ether. By the above procedure there was obtained 3.40 g of N-t-butyloxycarbonyl-O-benzyl-L-seryl-D-isoglutamine benzyl ester. m.p. 65°–66° C.; $[\alpha]_D^{23}+5.7°$ (c=0.5, ethanol); $Rf^1$-0.73.

Elemental analysis, for $C_{27}H_{35}O_7N_3$; Calcd. C, 63.14; H, 6.87; N, 8.18; Found C, 62.98; H, 6.93; N, 8.19.

(2) Benzyl 2-acetamido-4,6-O-benzylidene-3-O-(D-1-carboxyethyl)-2-deoxy-α-D-glucopyranoside (7.07 g, 15 m mols) and N-hydroxy-5-norbornene-2,3-dicarboximide (hereinafter briefly referred to as HONB) (3.22 g, 18 m mols) were dissolved in tetrahydrofuran (110 ml), and under ice-cooling, N,N′-dicyclohexylcarbodiimide (3.71 g, 18 m mols) was added. The reaction was conducted at 0° C. for 3 hours and at room temperature for 16 hours. The crystalline precipitate was removed, the solvent was distilled off under reduced pressure and the residue was recrystallized from ethyl acetatediethyl ether. By the above procedure there was obtained 7.42 g of benzyl 2-acetamido-4,6-O-benzylidene-3-O-(D-1-carboxyethyl)-2-deoxy-α-D-glucopyranoside HONB-activated ester. m.p. 122°–124° C.

(3) N-t-butyloxycarbonyl-O-benzyl-L-seryl-D-isoglutamine benzyl ester (5.0 g, 10 m mols) was dissolved in trifluoroacetic acid (25 ml) and the solution was allowed to stand at room temperature for 20 minutes. The trifluoroacetic acid was distilled off, petroleum ether-diethyl ether (1:1) was added to the residue and the precipitate was recovered by filtration and dissolved in N,N-dimethylformamide (20 ml). Under ice-cooling, triethylamine (1.60 ml) and benzyl 2-acetamido-4,6-O-benzylidene-3-O-(D-1-carboxyethyl)-2-deoxy-α-D-glucopyranoside HONB-activated ester (6.35 g, 10 m mols) dissolved in acetonitrile (50 ml) were added to the above dimethylformamide solution. The mixture was allowed to stand at room temperature for 60 hours, at the end of which time diethyl ether (100 ml) was added. The resultant crystals were recovered by filtration and recrystallized from N,N-dimethylformamide-acetonitrile. By the above procedure there was obtained 7.60 g of benzyl 2-(benzyl 2-acetamido-4,6-O-benzylidene-2-deoxy-α-D-glucopyranosid-3-O-yl)-D-propionyl-O-benzyl-L-seryl-D-isoglutaminate. m.p. 259° C. (decomp.): $[\alpha]_D^{23}+81.1°$ (c=0.5, N,N-dimethylformamide); $Rf^1=0.69$.

Elemental analysis, for $C_{47}H_{54}O_{12}N_4$; Calcd. C, 65.11; H, 6.28; N, 6.46; Found C, 65.23; H, 6.21; N, 6.40.

(4) Benzyl 2-(benzyl 2-acetamido-4,6-O-(benzylidene-2-deoxy-α-D-glucopyranosid-3-O-yl)-D-propionyl-O-benzyl-L-seryl-D-isoglutaminate (7.50 g, 8.65 m mols) was dissolved in 75% acetic acid under heating at 100° C. and the solution was further heated at 100° C. for one hour. The solvent was then distilled off and the crystalline residue was recrystallized from ethanol-diethyl ether. By the above procedure there was obtained 4.48 g of benzyl 2-(benzyl 2-acetamido-2-deoxy-α-D-glucopyranosid-3-O-yl)-D-propionyl-O-benzyl-L-seryl-D-isoglutaminate. m.p. 188°–191° C.; $[\alpha]_D^{23}+89.8°$ (c=0.5, N,N-dimethylformamide); $Rf^1=0.31$.

Elemental analysis, for $C_{40}H_{50}O_{12}N_4.\frac{1}{2}H_2O$; Calcd. C, 60.98; H, 6.53; N, 7.11; Found C, 61.07; H, 6.38; N, 7.00.

(5) Benzyl 2-(benzyl 2-acetamido-2-deoxy-α-D-glucopyranosid-3-O-yl)-D-propionyl-O-benzyl-L-seryl-D-isoglutaminate (3.12 g, 4 m mols), carbobenzoxy-L-leucine p-nitrophenyl ester (2.32 g, 6 m mols), N-ethylmorpholine (1.54 ml, 12 m mols) and 1-hydroxybenzotriazole (1.62 g, 12 m mols) were dissolved in N,N-dimethylformamide (10 ml) and the reaction was conducted at room temperature for 90 hours. The reaction mixture was diluted with water (100 ml) and extracted with ethyl acetate (150 ml). The ethyl acetate layer was washed with 1 N-aqueous ammonia, 1 N-hydrochloric acid and water in the order mentioned and dried over anhydrous sodium sulfate. The solvent was distilled off and the residue was purified by silica gel column chromatography, elution being carried out with chloroform-methanol (19:1). By the above procedure there was obtained 2.55 g of benzyl 2-[benzyl 2-acetamido-6-O-(carbobenzoxy-L-leucyl)-2-deoxy-α-D-glucopyranosid-3-O-yl]-D-propionyl-O-benzyl-L-seryl-D-isoglutaminate as crystals melting at 177°–178° C. $[\alpha]_D^{23}+58.7°$ (c=0.5, N,N-dimethylformamide); $Rf^1=0.70$.

Elemental analysis, for $C_{54}H_{67}O_{15}N_5$; Calcd. C, 63.20; H, 6.58; N, 6.83; Found C, 63.01; H, 6.49; N, 6.71.

(6) With palladium black as a catalyst, benzyl 2-[benzyl 2-acetamido-6-O-(carbobenzoxy-L-leucyl)-2-deoxy-α-D-glucopyranosid-3-O-yl]-D-propionyl-O-benzyl-L-seryl-D-isoglutaminate (2.00 g, 1.95 m mols) was hydrogenated in acetic acid (30 ml) for 12 hours. After the catalyst was removed, the solvent was distilled off and the residue was reprecipitated from ethanol-diethyl ether. By the above procedure there was obtained 1.22 g of 2-(2-acetamido-2-deoxy-6-O-L-leucyl-D-glucos-3-O-yl)-D-propionyl-L-seryl-D-isoglutamine. m.p. 154° C. (decomp.); $[\alpha]_D^{23}+21.0°$ (after 3 min.)→+28.8° (after 25 hrs.) (c=0.5, water); $Rf^2=0.55$.

Elemental analysis, for $C_{25}H_{43}O_{13}N_5.H_2O$; Calcd. C, 46.93; H, 7.09; N, 10.94; Found C, 47.00; H, 7.19; N, 10.52.

EXAMPLE 6

(1) In N,N-dimethylformamide (4 ml), benzyl 2-(benzyl 2-acetamido-2-deoxy-α-D-glucopyranosid-3-O-yl)-D-propionyl-L-alanyl-D-isoglutaminate (505 mg, 0.75 m mols) and α-t-butyloxycarbonyl-ε-carbobenzoxy-L-lysine p-nitrophenyl ester (752 mg, 1.5 m m mols) were reacted in the presence of 1-hydroxybenzotriazole (405 mg, 3 m mols) and N-ethylmorpholine (0.384 ml, 3 m mols) at room temperature for 2 days and the reaction product was purified as in Example 1-(1). The product was further precipitated as a gel by ethanol-ethyl acetate-diethyl ether. By the above procedure there was obtained 552 mg of benzyl 2-[benzyl 2-acetamido-6-O-(α-t-butyloxycarbonyl-ε-carbobenzoxy-L-lysyl)-2-deoxy-α-D-glucopyranosid-3-O-yl]-D-propionyl-L-alanyl-D-isoglutaminate, m.p. 164°–165° C.; $[\alpha]_D^{23}+62.8°$ (c=0.5, N,N-dimethylformamide); $Rf^1=0.54$.

Elemental analysis, for $C_{52}H_{70}O_{16}N_6$; Calcd. C, 60.33; H, 6.82; N, 8.12; Found C, 59.95; H, 6.75; N, 7.97.

(2) In trifluoroacetic acid (5 ml) was dissolved benzyl 2-[benzyl 2-acetamido-6-O-(α-t-butyloxycarbonyl-ε-carbobenzoxy-L-lysyl)-2-deoxy-α-D-glucopyranosid-3-O-yl)-D-propionyl-L-alanyl-D-isoglutaminate (155 mg, 0.15 m mol) and, after being stirred at room temperature for 15 minutes, the solution was concentrated under reduced pressure. Following addition of diethyl ether, the precipitate was recovered by filtration. By the above procedure there was obtained benzyl 2-[benzyl 2-acetamido-6-O-(ε-carbobenzoxy-L-lysyl)-2-deoxy-α-D-glucopyranosid-3-O-yl]-D-propionyl-L-alanyl-D-isoglutaminate trifluoroacetate in quantitative yield, $Rf^1=0.26$ (3) In the same manner as Example 1-(2), the above benzyl 2-[benzyl 2-acetamido-6-O-(ε-carbobenzoxy-L-lysyl)-2-deoxy- α-D-glucopyranosid-3-O-yl]-D-propionyl-L-alanyl-D-isoglutaminate trifluoroacetate was hydrogenated in acetic acid with the aid of palladium black as a catalyst and the reaction product was purified. By the above procedure there was obtained 91 mg of 2-(2-acetamido-2-deoxy-6-O-L-lysyl-D-glucos-3-O-yl)-D-propionyl-L-alanyl-D-isoglutamine acetate m.p. 74°–76° C.; $[\alpha]_D^{23}+38.6°$ (c=0.5, N,N-dimethylformamide); $Rf^2=0.20$.

Elemental analysis, for $C_{25}H_{44}O_{12}N_6 \cdot 2CH_3COOH \cdot 6H_2O$; Calcd. C, 41.03; H, 7.60; N, 9.90; Found C, 41.03; H, 6.79; N, 9.98.

EXAMPLE 7

(1) t-Butyloxycarbonyl-α-aminoisobutyric acid (0.96 g, 4.7 m mols) and HONB (1.00 g, 5.6 m mols) were dissolved in acetonitrile (10 ml), and under ice-cooling, N,N'-dicyclohexylcarbodiimide (1.16 g, 5.6 m mols) was added. The reaction was conducted at 4° C. for 16 hours. The resultant crystals were removed, the solvent was distilled off under reduced pressure and the residue was added to 10 ml of a solution of D-isoglutamine benzyl ester (1.11 g, 4.7 m mols) in N,N-dimethylformamide and the reaction was conducted at room temperature for 16 hours. The solvent was distilled off and the residue was dissolved in ethyl acetate and washed with 1 N hydrochloric acid, 5% aqueous sodium hydrogen carbonate and saturated aqueous sodium chloride in the order mentioned. The organic layer was dried over anhydrous sodium sulfate, the solvent was distilled off and the residue was recrystallized from ethyl acetate-diethyl ether. By the above procedure there was obtained 1.39 g of t-butyloxycarbonyl-α-aminoisobutyroyl-D-isoglutamine benzyl ester as crystals melting at 112°–113° C.

In trifluoroacetic acid (7 ml) was dissolved the above t-butyloxycarbonyl-α-aminoisobutyroyl-D-isoglutamine benzyl ester (632 mg, 1.5 m mols) and the reaction was conducted at room temperature for 30 minutes. The solvent was distilled off and diethyl ether was added to the residue. The precipitated α-aminoisobutyroyl-D-isoglutamine benzyl ester trifluoroacetate was recovered by filtration. It was dissolved in tetrahydrofuran (10 ml) and, under ice-cooling neutralized with triethylamine (0.21 ml). By the above procedure there was obtained a solution of α-aminoisobutyroyl-D-isoglutamine benzyl ester in tetrahydrofuran.

(2) The α-aminoisobutyroyl-D-isoglutamine benzyl ester solution obtained in (1) was admixed with 10 ml of a tetrahydrofuran solution of the benzyl 2-acetamido-4,6-O-benzylidene-3-O-(D-1-carboxyethyl)-2-deoxy-α-D-glucopyranoside HONB ester (949 mg, 1.5 m mols) and the reaction was conducted at room temperature for 16 hours. The reaction mixture was concentrated and the resultant precipitate was recovered by filtration. By the above procedure there was obtained 457 mg of benzyl 2-(benzyl 2-acetamido-4,6-O-benzylidene-2-deoxy-α-D-glucopyranosid-3-O-yl)-D-propionyl-α-aminoisobutyroyl-D-isoglutaminate, $Rf^1=0.70$ Elemental analysis, for $C_{41}H_{50}O_{11}N_4$; Calcd. C, 63.55; H, 6.51; N, 7.23; Found C, 63.82; H, 6.88; N, 6.87.

(3) In 20 ml of 60% acetic acid was dissolved benzyl 2-(benzyl 2-acetamido-4,6-O-benzylidene-2-deoxy-α-D-glucopyranosid-3-O-yl)-D-propionyl-α-aminoisobutyroyl-D-isoglutaminate (973 mg, 1.26 m mols) and the solution was heated on a boiling water bath for 30 minutes. After the reaction, the solvent was distilled off, and the residue was dissolved in ethyl acetate and precipitated by the addition of diethyl ether. By the above procedure there was obtained 505 mg of benzyl 2-(benzyl 2-acetamido-2-deoxy-α-D-glucopyranosid-3-O-yl)-D-propionyl-α-aminobutyroyl-D-isoglutaminate.

$[\alpha]_D^{23}+9.8°$ (c=1.0, ethanol); Rf=0.46 [chloroform-acetone-methanol=10:3:2; silica gel plate].

Elemental analysis, for $C_{34}H_{46}O_{11}N_4 \cdot H_2O$; Calcd. C, 57.94; H, 6.87; N, 7.95; Found C, 58.07; H, 6.77; N, 7.89.

(4) In the same manner as Example 2-(1), benzyl 2-(benzyl 2-acetamido-2-deoxy-α-D-glucopyranosid-3-O-yl)-D-propionyl-α-aminoisobutyroyl-D-isoglutaminate (412 mg, 0.6 m mol) and carbobenzoxy-glycine p-nitrophenyl ester were reacted in N,N-dimethylformamide (3 ml) and in the presence of 1-hydroxybenzotriazole (324 mg, 2.4 m mols) and N-ethylmorpholine (0.31 ml, 2.4 m mols). This reaction was conducted at room temperature for 40 hours and the reaction product was similarly purified. By the above procedure there was obtained 356 mg of benzyl 2-[benzyl 2-acetamido-6-O-(carbobenzoxy-glycyl)-2-deoxy-α-D-glucopyranosid-3-O-yl]-D-propionyl-α-aminoisobutyroyl-D-isoglutaminate. m.p. 67° C. (decomp.); $[\alpha]_D^{23}+75.8°$ (c=0.5, N,N-dimethylformamide); $Rf^1=0.54$.

Elemental analysis, for $C_{44}H_{55}O_{14}N_5$; Calcd. C, 60.19; H, 6.32; N, 7.98; Found C, 60.25; H, 6.25; N, 7.95.

(5) In the same manner as Example 1-(2), benzyl 2-[benzyl 2-acetamido-6-O-(carbobenzoxy-glycyl)-2-deoxy-α-D-glucopyranosid-3-O-yl]-D-propionyl-α-aminoisobutyroyl-D-isoglutaminate (307 mg, 0.55 m mol) was hydrogenated in acetic acid with the aid of palladium black and the reaction product was purified. By the above procedure there was obtained 184 mg of 2-(2-acetamido-2-deoxy-6-O-glycyl-D-glucos-3-O-yl)-D-propionyl-α-aminoisobutyroyl-D-isoglutamine. m.p. 128° C. (decomp.); $[\alpha]_D^{23}+61.0°$ (c=0.5, N,N-dimethylformamide); $Rf^2=0.44$.

Elemental analysis, for $C_{22}H_{37}O_{12}N_5 \cdot \frac{1}{2}H_2O$; Calcd. C, 46.15; H, 6.69; N, 12.23; Found C, 46.26; H, 6.93; N, 12.29.

EXAMPLE 8

(1) Benzyl 2-(benzyl 2-acetamido-2-deoxy-α-D-glucopyranosid-3-O-yl)-D-propionyl-α-aminoisobutyroyl-D-isoglutaminate (493 mg, 0.72 m mol) and carbobenzoxy-ε-amino-n-caproic acid p-nitrophenyl ester (580 mg, 1.5 m mols) were reacted in N,N-dimethylformamide and in the presence of 1-hydroxybenzotriazole (405 mg, 3 m mols) and N-ethylmorpholine (0.38 ml, 3 m mols) at room temperature for 4 days and the reaction product was purified in the same manner as Example 3-(1). By the above procedure there was obtained 422 mg of benzyl 2-[benzyl 2-acetamido-6-O-(carbobenzoxy-ε-amino-n-caproyl)-2-deoxy-α-D-glucopyranosid-3-O-yl]-D-propionyl-α-aminoisobutyroyl-D-isoglutaminate. m.p. 62°–64° C.; $[\alpha]_D^{23}+70.2°$ (c=0.5, N,N-dimethylformamide); $Rf^1=0.59$.

Elemental analysis, for $C_{48}H_{63}O_{14}N_5$; Calcd. C, 61.72; H, 6.80; N, 7.50; Found C, 61.55; H, 6.70; N, 7.61.

(2) In the same manner as Example 1-(2), 374 mg of benzyl 2-[benzyl 2-acetamido-6-O-(carbobenzoxy-ε-amino-n-caproyl)-2-deoxy-α-D-glucopyranosid-3-O-yl]-D-propionyl-α-aminoisobutyroyl-D-isoglutaminate was hydrogenated in acetic acid with the aid of palladium black and the reaction product was purified. By the above procedure there was obtained 202 mg of 2-[2-acetamido-6-O-(ε-amino-n-caproyl)-2-deoxy-D-glucos-3-O-yl]-D-propionyl-α-aminoisobutyroyl-D-isoglutamine. m.p. 98°–100° C. (decomp.); $[\alpha]_D^{23}+70.0°$ (c=0.5, N,N-dimethylformamide); $Rf^2=0.45$.

Elemental analysis, for $C_{26}H_{45}O_{12}N_5 \cdot H_2O$; Calcd. C, 48.97; H, 7.43; N, 10.98; Found C, 49.00; H, 7.91; N, 10.71.

EXAMPLE 9

(1) In a 2 N-aqueous solution of sodium hydroxide (500 ml) was dissolved 11-aminoundecanoic acid (30.2 g, 0.15 mol) under mild heating (50° C.). With intense stirring, carbobenzoxy chloride (30.7 g, 0.18 mol) was added in 4 installments over a period of 30 minutes, after which the mixture was stirred for 2 hours. The reaction mixture was cooled with ice, adjusted to pH 2 with 6 N-hydrochloric acid and extracted with ethyl acetate (600 ml). The ethyl acetate layer was washed with water and dried over anhydrous sodium sulfate. The solvent was distilled off and petroleum ether was added to the crystalline residue. After cooling, the crystals were recovered by filtration. By the above procedure there was obtained 36.0 g of N-carbobenzoxy-11-aminoundecanoic acid. m.p. 96°–97° C.; $Rf^1 = 0.67$.

Elemental analysis, for $C_{19}H_{29}O_4N$; Calcd. C, 68.03; H, 8.71; N, 4.18; Found C, 68.05; H, 8.73; N, 3.78.

(2) In a solvent mixture (120 ml) of ethyl acetate and N,N-dimethylformamide (5:1) was dissolved N-carbobenzoxy-11-aminoundecanoic acid (10.1 g, 30 m mols) and p-nitrophenol (4.59 g, 33 m mols), followed by addition of N,N'-dicyclohexylcarbodiimide (6.80 g, 33 m mols). The mixture was stirred at room temperature for 15 hours, after which the precipitate was filtered off. The solvent was distilled off and the residue was crystallized in petroleum ether, recovered by filtration and recrystallized from ethyl acetate-petroleum ether. By the above procedure there was obtained 7.65 g of N-carbobenzoxy-11-aminoundecanoic acid p-nitrophenyl ester. m.p. 72°–73° C.; $Rf^1 = 0.94$.

Elemental analysis, for $C_{25}H_{32}O_6N_2$; Calcd. C, 65.77; H, 7.07; N, 6.14; Found C, 66.03; H, 7.17; N, 6.18.

(3) In N,N-dimethylformamide (25 ml), benzyl 2-(benzyl. 2-acetamido-2-deoxy-α-D-glucopyranosid-3-O-yl)-D-propionyl-L-alanyl-D-isoglutaminate (2.01 g, 3 m mols) and N-carbobenzoxy-11-aminoundecanoic acid p-nitrophenyl ester (2.74 g, 6 m mols) were reacted in the pressure of 1-hydroxybenzotriazole (1.62 g, 12 m mols) and N-ethylmorpholine (1.54 ml, 12 m mols) at room temperature for 2 days and the reaction product was purified as in Example 3-(1). By the above procedure there was obtained 1.76 g of benzyl 2-[benzyl 2-acetamido-6-O-(N-carbobenzoxy-11-aminoundecanoyl)-2-deoxy-α-D-glucopyranosid-3-O-yl]-D-propionyl-L-analyl-D-isoglutaminate, m.p. 144°–145° C.; $Rf^1 = 0.66$; $[α]_D^{21} + 67.3°$ (c=0.5, N,N-dimethylformamide).

Elemental analysis, for $C_{52}H_{71}O_{14}N_5$; Calcd. C, 63.07; H, 7.23; N, 7.07; Found C, 63.18; H, 7.31; N, 6.97.

(4) In the same manner as Example 1-(2), benzyl 2-[benzyl 2-acetamido-6-O-(N-carbobenzoxy-11-aminoundecanoyl)-2-deoxy-α-D-glucopyranosid-3-O-yl]-D-propionyl-L-alanyl-D-isoglutaminate (1.70 g, 1.72 m mols) was hydrogenated in acetic acid with the aid of palladium black as a catalyst and the reaction product was purified. By the above procedure there was obtained 1.02 g of 2-[2-acetamido-6-O-(11-aminoundecanoyl)-2-deoxy-D-glucos-3-O-yl]-D-propionyl-L-alanyl-D-isoglutamine. m.p. 120° C. (decomp.); $Rf^2 = 0.61$; $[α]_D^{21} + 20.7°$ (c=0.5, N,N-dimethylformamide).

Elemental analysis, for $C_{30}H_{53}O_{12}N_5 \cdot H_2O$; Calcd. C, 51.93; H, 7.99; N, 10.10; Found C, 51.85; H, 8.00; N, 9.82.

EXAMPLE 10

(1) t-Butyloxycarbonyl-L-valyl-D-isoglutamine benzyl ester was produced in a manner similar to Example 7-(1). m.p. 149°–151° C.; $[α]_D^{22} + 5.6°$ (c=0.5, N,N-dimethylformamide); $Rf^1 = 0.80$.

Elemental analysis, for $C_{22}H_{33}O_6N_3$; Calcd. C, 60.67; H, 7.64; N, 9.65; Found C, 60.53; H, 7.74; N, 9.54.

(2) Benzyl 2-(benzyl 2-acetamido-4,6-O-benzylidene-2-deoxy-α-D-glucopyranosid-3-O-yl)-D-propionyl-L-valyl-D-isoglutaminate was produced in a manner similar to Example 7-(2) m.p. >280° C., $[α]_D^{22} + 89.2°$ C. (c=0.5, N,N-dimethylformamide), $Rf^1 = 0.79$.

Elemental analysis, for $C_{42}H_{52}O_{11}N_4$; Calcd. C, 63.94; H, 6.64; N, 7.10; Found C, 63.81; H, 6.84; N, 6.99.

(3) Benzyl 2-(benzyl 2- acetamido-2-deoxy-α-D-glucopyranosid-3-O-yl)-D-propionyl-L-valyl-D-isoglutaminate was produced in a manner similar to Example 7-(3). m.p. 245°–248° C. (dec.) $[α]_D^{25} + 99.6°$ (c=0.5, N,N-dimethylformamide); $Rf^1 = 0.31$.

Elemental analysis, for $C_{35}H_{48}O_{11}N_4$; Calcd. C, 59.22; H, 6.96; N, 7.89; Found C, 59.39; H, 6.90; N, 7.82.

(4) Benzyl 2-[benzyl 2-acetamido-6-O-(carbobenzoxyglycyl)-2-deoxy-α-D-glucopyranosid-3-O-yl]-D-propionyl-L-valyl-D-isoglutaminate was produced in a manner similar to Example 7-(4). m.p.: 188°–191° C., $[α]_D^{22} + 72.6°$ (c=0.5, ethanol); $Rf^1 + 0.63$.

Elemental analysis, for $C_{45}H_{57}O_{14}N_5$; Calcd. C, 60.60; H, 6.44; N, 7.85; Found C, 60.22; H, 6.42; N, 7.72.

(5) 2-(2-Acetamido-2-deoxy-6-O-glycyl-D-glucos-3-O-yl)-D-propionyl-L-valyl-D-isoglutamine was produced in a manner similar to Example 7-(5). $[α]_D^{22} + 35.6°$ (c=0.5, ethanol), $Rf^2 = 0.44$.

Elemental analysis, for $C_{23}H_{39}O_{12}N_5 \cdot H_2O$; Calcd. C, 46.38; H, 6.94; N, 11.76; Found C, 45.99; H, 6.84; N, 11.53.

EXAMPLE 11

2-(2-Acetamido-2-deoxy-6-O-L-leuzyl-D-glucos-3-O-yl)-D-propionyl-α-aminoisobutyroyl-D-isoglutamine was produced in a manner similar to Example 7. m.p. 150°–153° C. (dec.): $[α]_D^{20} + 56.9°$ (c=0.5, N,N-dimethylformamide); $Rf^2 = 0.47$ Elemental analysis, for $C_{26}H_{45}O_{12}N_5 \cdot 3H_2O$; Calcd. C, 46.35; H, 7.63; N, 10.40; Found C, 46.14; H, 7.45; N, 10.20.

EXAMPLE 12

2-(2-Acetamido-2-deoxy-6-O-D-leucyl-D-glucos-3-O-yl)-D-propionyl-α-aminoisobutyroyl-D-isoglutamine was produced in a manner similar to Example 7. m.p. 145°–147° C.; $[α]_D^{20} + 50.2°$ (c=0.5, N,N-dimethylformamide); $Rf^2 = 0.47$.

Elemental analysis, for $C_{26}H_{45}O_{12}N_5 \cdot 3H_2O$; Calcd. C, 46.35; H, 7.63; N, 10.40; Found C, 46.08; H, 7.32; N, 10.06.

EXAMPLE 13

2-[2-Acetamido-2-deoxy-6-O-(11-aminoundecanoyl)-D glucos-3-O-yl]-D-propionyl-α-aminoisobutyroyl-D-isoglutamine was produced in a manner similar to Example 9, m.p. 119°–120° C.; $[α]_D^{20} + 57.2°$ (c=0.5, N,N-dimethylformamide); $Rf^2 = 0.55$.

Elemental analysis, for $C_{31}H_{55}O_{12}N_5 \cdot H_2O$; Calcd. C, 51.29; H, 8.19; N, 9.65; Found C, 51.31; H, 8.18; N, 9.55.

EXAMPLE 14

2-(2-Acetamido-2-deoxy-6-O-L-leucyl-D-glucos-3-O-yl)-D-propionyl-L-valyl-D-isoglutamine was produced in a manner similar to Example 10, m.p. 136°-138° C. (dec.) $[\alpha]_D^{25}+45.6°$ (c=0.5, N,N-dimethylformamide); $Rf^2=0.58$.

Elemental analysis, for $C_{27}H_{42}O_{12}N_5 \cdot H_2O$; Calcd. C, 49.76; H, 7.58; N, 10.74; Found C, 49.98; H, 7.94; N, 10.79.

EXAMPLE 15

(1) Geranylacetic acid (393 mg, 2 m mols) and p-nitrophenol (306 mg, 2.2 m mols) were dissolved in 4 ml of acetonitrile, and under ice-cooling, N,N'-dicyclohexylcarbodiimide (494 mg, 2.4 m mols) was added. The mixture was stirred at 0° C. for one hour and at room temperature for 1.5 hours. The resultant crystals were removed and the solvent was distilled off under reduced pressure, whereby gelanylacetic acid p-nitrophenyl ester was obtained as an oil.

(2) 6-O-β-alanyl-N-acetylmuramyl-L-alanyl-D-isoglutamine (564 mg, 1 m mol) obtained in Example 2-(2) and geranylacetic acid p-nitrophenyl ester (317 mg, 1.2 m mols) were dissolved in N,N-dimethylformamide (15 ml) and, following addition of N-ethylmorpholine (0.128 ml), the solution was stirred at room temperature for 17 hours. The solvent was distilled off under reduced pressure, the residue was dissolved in a small amount of ethanol and acetic acid (0.1 ml) was added. Then, diethyl ether was added. After cooling, the precipitate was recovered by filtration (700 mg). This precipitate was applied onto a column Sephadex LH-20 and elution was carried out with 30% ethanol. By this purification procedure there was obtained 415 mg of 2-[2-acetamido-2-deoxy-6-O-(geranylacetyl-β-alanyl)-D-glucos-3-O-yl]-D-propionyl-L-alanyl-D-isoglutamine. $[\alpha]_D^{24}+29.9°$ (after 3 min.)→28.2° (after 25 hrs.) [c=0.77, water]; $Rf^2=0.65$; $Rf=0.47$ (ethyl acetate-pyridine-acetic acid-water=30:10:3:5, silica gel plate) (The Rf values found under the above conditions will be designated by the symbol $Rf^3$.)

Elemental analysis, for $C_{34}H_{55}O_{13}N_5 \cdot H_2O$; Calcd. C, 53.74; H, 7.56; N, 9.21; Found C, 53.31; H, 7.43; N, 8.96.

(3) In 2 ml of water was dissolved 2-[2-acetamido-2-deoxy-6-O-(geranylacetyl-β-alanyl)-D-glucos-3-O-yl]-D-propionyl-L-alanyl-D-isoglutamine (150 mg, 0.2 m mol) and, under ice-cooling and stirring, the solution was brought to pH 7 by the dropwise addition of 0.5 N-sodium hydroxide. The solution was freeze-dried a couple of times, whereby 162 mg of the Na salt of 2-[2-acetamido-2-deoxy-6-O-(geranylacetyl-β-alanyl)-D-glucos-3-O-yl]-D-propionyl-L-alanyl-D-isoglutamine was obtained.

Elemental analysis, for $C_{34}H_{54}O_{13}N_5Na \cdot 2H_2O$; Calcd. C, 51.06; H, 7.31; N, 8.76; Found C, 50.81; H, 7.66; N, 8.21.

EXAMPLE 16

(1) Digeranylacetic acid (300 mg, 0.9 m mol) and p-nitrophenol (139 mg, 1 m mol) were dissolved in acetonitrile-ethyl acetate (1:1) (10 ml), and under ice-cooling, N,N'-dicyclohexylcarbodiimide (227 mg, 1.1 m mols) was added. The mixture was stirred at 0° C. for 3 hours and at room temperature for 15 hours. The crystalline precipitate was removed and the solvent was distilled off under reduced pressure, whereby digeranyl acetic acid p-nitrophenyl ester was obtained.

(2) The above digeranylacetic acid p-nitrophenyl ester and 6-O-β-alanyl-N-acetylmuranyl-L-alanyl-D-isoglutamine (423 mg, 0.75 m mol) were dissolved in N,N-dimethylformamide (10 ml), followed by addition of N-ethylmorpholine (0.1 ml). The mixture was reacted at room temperature for 2 days. The solvent was then distilled off under reduced pressure, the residue was dissolved in ethanol and the small amount of insolubles was filtered off. To the filtrate was added acetic acid (0.1 ml), followed by addition of diethyl ether. The precipitate was recovered by filtration (500 mg). This precipitate was applied onto a column of silica gel, elution being carried out with ethyl acetate-pyridine-acetic acid-water (30:10:3:5). The fractions rich in the principal product were pooled and concentrated under reduced pressure to about 5 ml. The concentrate was diluted with 100 ml of water and freeze-dried. The residue (130 mg) was purified by means of a column of Sephadex LH-20, with ethanol as an eluent. By the above procedure there was obtained 91 mg of 2-[(2-acetamido-6-O-(digeranylacetyl-β-alanyl)-2-deoxy-D-glucos-3-O-yl]-D-propionyl-L-alanyl-D-isoglutamine. $[\alpha]_D^{24}+25.0°$ (after 3 min.)→+24.7° (after 24 hrs.) [c=0.32, water]; $Rf^2=0.80$; $Rf^3=0.59$.

Elemental analysis, for $C_{44}H_{71}O_{13}N_5 \cdot H_2O$; Calcd. C, 57.48; H, 7.82; N, 7.45; Found C, 57.07; H, 7.81; N, 7.67.

EXAMPLE 17

(1) Farnesylacetic acid (52.9 mg, 0.2 m mol) and HONB (39.4 mg, 0.22 m mol) were dissolved in acetonitrile (2 ml), and under ice-cooling, N,N'-dicyclohexylcarbodiimide (45.4 mg, 0.22 m mol) was added. The mixture was stirred at 0° C. for 2 hours and at room temperature for 13 hours. The resultant crystals were removed and the solvent was distilled off under reduced pressure. By the above procedure there was obtained farnesylacetic acid HONB ester as an oily residue.

(2) In N,N-dimethylformamide (4 ml) was dissolved the above farnesylacetic acid HONB ester, together with 6-O-β-alanyl-N-acetylmuramyl-L-alanyl-D-isoglutamine (112.7 mg, 0.2 m mol), followed by addition of N-ethylmorpholine (25.6 μl). The mixture was stirred at room temperature for 17 hours. The solvent was distilled off under reduced pressure, the residue was applied onto a column of silica gel and elution was carried out with ethyl acetate-pyridine-acetic acid-water (30:10:3:5). The fractions rich in the principal product was pooled and the solvent was distilled off under reduced pressure. The residue was applied to a column of Sephadex LH-20 and elution was carried out with ethanol-0.1 N acetic acid (3:2). By the above procedure there was obtained 80.2 mg of 2-[2-acetamido-2-deoxy-6-O-(farnesylacetyl-β-alanyl)-D-glucos-3-O-yl]-D-propionyl-L-alanyl-D-isoglutamine. $[\alpha]_D^{23}+38.4°$ (c=0.5, N,N-dimethylformamide); $Rf^2=0.72$; $Rf^3=0.53$.

Elemental analysis, for $C_{39}H_{63}O_{13}N_5 \cdot H_2O$; Calcd. C, 56.57; H, 7.91; N, 8.45; Found C, 56.24; H, 7.96; N, 8.43.

EXAMPLE 18

Geranylgeranylacetic acid (83.1 mg, 0.25 m mol), HONB (50.4 mg, 0.28 m mol) and N,N'-dicyclohexylcarbodiimide (57.7 mg, 0.28 m mol) were reacted in the same manner as Example 17-(1). The activated ester thus obtained and 6-O-β-alanyl-N-acetylmuramyl-L-alanyl-D-isoglutamine (141 mg, 0.25 m mol) were reacted in N,N-dimethylformamide (4 ml) and in the presence of N-ethylmorpholine (36 μl, 0.28 m mol) at room temperature under exclusion of light for 60 hours. The reaction product was purified as in Example 17-(2). By the above procedure there was obtained 74 mg of 2-[2-acetamido-2-deoxy-6-O-(geranylgeranylacetyl-$\beta$-alanyl)-D-glucos-3-O-yl)-L-propionyl-L-alanyl-D-isoglutamine. $[\alpha]_D^{27}+25.8°$ (c=0.3; 70% ethanol); $Rf^3=0.70$.

Elemental analysis, for $C_{44}H_{71}O_{13}N_5.2H_2O$; Calcd. C, 57.81; H, 8.27; N, 7.66; Found C, 57.59; H, 7.95; N, 7.62.

EXAMPLE 19

Di(geranylgeranyl)acetic acid (91 mg, 0.15 m mol), HONB (32.4 mg, 0.18 m mol) and N,N'-dicyclohexylcarbodiimide (37.1 mg, 0.18 m mol) were reacted in acetonitrile-ethyl acetate (1:1) (4 ml) as in Example 17-(1). The activated ester thus obtained and 6-O-$\beta$-alanyl-N-acetylmuramyl-L-alanyl-D-isoglutamine (85 mg, 0.15 m mol) were reacted in N,N-dimethylformamide (2.5 ml) and in the presence of N-ethylmorpholine (0.02 ml) at room temperature for 48 hours. The reaction product was purified in the same manner as in Example 17-(2) to recover 49 mg of 2-{2-acetamido-2-deoxy-6-O-[di-(geranylgeranyl)acetyl-$\beta$-alanyl]-D-glucos-3-O-yl}-D-propionyl-L-alanyl-D-isoglutamine. $[\alpha]_D^{27}+20.0°$ (c=0.3, 70% ethanol); $Rf^3=0.86$.

Elemental analysis, for $C_{64}H_{103}O_{13}N_5.2H_2O$; Calcd. C, 64.78; H, 9.09; N, 5.90; Found C, 64.58; H, 9.08; N, 6.00.

EXAMPLE 20

In N,N-dimethylformamide (10 ml) were dissolved stearic acid p-nitrophenyl ester (486 mg, 1.2 m mols) and 6-O-$\beta$-alanyl-N-acetylmuramyl-L-alanyl-D-isoglutamine (563.5 mg, 1 m mol), followed by addition of N-ethylmorpholine (0.18 ml). The mixture was stirred at room temperature for 17 hours. The solvent was distilled off under reduced pressure and the residue was slightly dissolved by the addition of ethyl acetate. Following addition of diethyl ether, the mixture was cooled and the precipitate was recovered by filtration and applied onto a column of silica gel. Elution was carried out with ethyl acetate-pyridine-acetic acid-water (100:30:9:15, V/V), whereby 550 mg of crude product was obtained.

A 70 mg portion of the above crude product was purified by means of a column of Sephadex LH-20, elution being carried out with ethanol-0.1 N acetic acid (3:2). By the above procedure there was obtained 60 mg of 2-[2-acetamido-2-deoxy-6-O-(stearyl-$\beta$-alanyl)-D-glucos-3-O-yl]-D-propionyl-L-alanyl-D-isoglutamine. $[\alpha]_D^{27}+22.4°$ (after 3 min.)→28.1° (after 25 hrs.) [c=0.5, 70% ethanol]; $Rf^3=0.67$.

Elemental analysis, for $C_{40}H_{71}O_{13}N_5.2H_2O$; Calcd. C, 55.47; H, 8.73; N, 8.09; Found C, 55.71; H, 8.88; N, 8.12.

EXAMPLE 21

Trans-13-docosenoic acid (101.6 mg, 0.3 m mol), HONB (59.1 mg, 0.33 m mol) and N,N'-dicyclohexylcarbodiimide (68.1 mg, 0.33 m mol) were reacted in acetonitrile as in Example 17-(1). The active ester thus obtained and 6-O-$\beta$-alanyl-N-acetylmuramyl-L-alanyl-D-isoglutamine (169.1 mg, 0.3 m mol) were reacted in N,N-dimethylformamide (3 ml) and in the presence of N-ethylmorpholine (38.4 $\mu$g, 0.3 m mol) at room temperature for 48 hours. The reaction product was purified as in Example 17-(2) to obtain 123.8 mg of 2-[2-acetamido-2-deoxy-6-O-(trans-13-docosenoyl-$\beta$-alanyl)-D-glucos-3-O-yl]-D-propionyl-L-alanyl-D-isoglutamine $[\alpha]_D^{23}+32.2°$ (c=1.0, ethanol); $Rf^2=0.77$, $Rf^3=0.61$.

Elemental analysis, for $C_{44}H_{77}O_{13}N_5.3/2H_2O$; Calcd. C, 58.00; H, 8.85; N, 7.67; Found C, 58.11; H, 8.83; N, 7.65.

EXAMPLE 22

3-(2,3-Dimethoxy-5-methyl-1,4-benzoquinon-6-yl)propionic acid (76.3 mg, 0.3 m mol) and HONB (59.1 mg, 0.3 m mol) were dissolved in acetonitrile (3 ml), and under ice-cooling, N,N-dicyclohexylcarbodiimide (68.1 mg, 0.3 m mol) was added. The mixture was reacted at 0° C. for one hour and at room temperature for 4 hours. The resultant crystals were removed and the solvent was distilled off under reduced pressure. The active ester thus obtained and 6-O-$\beta$-alanyl-N-acetylmuramyl-L-alanyl-D-isoglutamine (169.1 mg, 0.3 m mol) were dissolved in N,N-dimethylformamide (3 ml), and following addition of N-ethylmorpholine (38.4 $\mu$l, 0.3 m mol), the mixture was stirred at room temperature for 17 hours. The reaction product was purified in the same manner as in Example 17-(2). By the above procedure there was obtained 134 mg of 2-{2-acetamido-2-deoxy-6-O-[3-(2,3-dimethoxy-5-methyl-1,4-benzoquinon-6-yl)-propionyl-$\beta$-alanyl]-D-glucos-3-O-yl}-D-propionyl-L-alanyl-D-isoglutamine. The reaction and all treatments thereafter were carried out in the dark. $[\alpha]_L^{23}+31.2°$ (c=0.5, N,N-dimethylformamide); $Rf^2=0.63$; $Rf^3=0.34$.

Elemental analysis, for $C_{34}H_{49}O_{17}N_5.3H_2O$; Calcd. C, 47.82; H, 6.49; N, 8.20; Found C, 47.66; H, 6.11; N, 8.23.

EXAMPLE 23

10-(2,3-Dimethoxy-5-methyl-1,4-benzoquinon-6-yl)decanoic acid (70.5 mg, 0.2 m mol), p-nitrophenol (30.6 mg, 0.22 m mol) and N,N'-dicyclohexylcarbodiimide (45.4 mg, 0.22 m mol) were reacted in acetonitrile (4 ml) as in Example 15-(1). The active ester thus obtained and 6-O-$\beta$-alanyl-N-acetylmuramyl-L-alanyl-D-isoglutamine (112.7 mg, 0.2 m mol) were reacted in N,N-dimethylformamide (4 ml) and in the presence of N-ethylmorpholine (25.6 $\mu$l, 0.2 m mol) at room temperature for 24 hours. The solvent was distilled off under reduced pressure and the residue was applied onto a column of Sephadex LH-20, elution being carried out with ethanol-0.1 N acetic acid (3:2). By the above procedure there was obtained 96 mg of 2-{2-acetamido-2-deoxy-6-O-[10-(2,3-dimethoxy-5-methyl-1,4-benzoquinon-6-O-yl)decanoyl-$\beta$-alanyl]-D-glucos-3-O-yl}-D-propionyl-L-alanyl-D-isoglutamine. The reaction and all treatments thereafter were carried out in the dark. $[\alpha]_D^{23}+29.0°$ (c=0.5, ethanol); $Rf^2=0.72$; $Rf^3=0.42$ Elemental analysis, for $C_{41}H_{63}O_{17}N_5.H_2O$; Calcd. C, 54.29; H, 7.22; N, 7.72; Found C, 54.13; H, 7.21; N, 7.50.

EXAMPLE 24

Retinoic acid [3,7-dimethyl-9-(2,6,6-trimethyl-1-cyclohexen-1-yl)-2,4,6,8-nonatetraenoic acid] (150.2 mg, 0.5 m mol) and HONB (104.4 mg, 0.58 m mol) were dissolved in a 1:1 mixture (4 ml) of acetonitrile and ethyl acetate, followed by addition of N,N'-dicyclohexylcarbodiimide (119.5 mg, 0.58 m mol) under ice-cooling. The mixture was stirred at 4° C. for 17 hours, after which the resultant crystals were removed and the solvent was distilled off. The active ester thus obtained and 6-O-β-alanyl-N-acetylmuramyl-L-alanyl-D-isoglutamine (282 mg, 0.5 m mol) were dissolved in 6 ml of N,N-dimethylformamide followed by the addition of N-ethylmorpholine (0.1 ml). The reaction was conducted at 4° C. for 48 hours. The reaction product was purified as in Example 20. By the above procedure there was obtained 115 mg of 2-[2-acetamido-2-deoxy-6-O-(retinoyl-β-alanyl)-D-glucos-3-O-yl]-D-propionyl-L-alanyl-D-isoglutamine. The reaction and all subsequent treatments were carried out in the dark. $[\alpha]_D^{27}+21.6°$ (after 3 min.)→23.9° (after 25 hrs.) [c=0.5, water]; $Rf^3=0.41$.

Elemental analysis, for $C_{42}H_{63}O_{13}N_5 \cdot 5H_2O$; Calcd. C, 53.85; H, 7.86; N, 7.48; Found C, 53.47; H, 7.19; N, 7.43.

EXAMPLE 25

(1) In 20 ml of acetonitrile were dissolved methacrylic acid (1.72 g, 20 m mols) and N-hydroxysuccinimide (2.19 g, 19 m mols), and under ice-cooling, N,N'-dicyclohexylcarbodiimide (4.33 g, 21 m mols) was added. The reaction was conducted in the dark, at 0° C. for one hour and at room temperature for 3 hours. The precipitate was separated by filtration and the filtrate was distilled under reduced pressure. To the residue was added petroleum ether and, after cooling, the crystals were collected by filtration. By the above procedure there was obtained 2.5 g of methacrylic acid N-hydroxysuccinimide ester as crystals melting at 100°-102° C.

Elemental analysis, for $C_8H_9O_4N$; Calcd. C, 52.45; H, 4.95; N, 7.65; Found C, 52.46; H, 4.83; N, 8.05.

(2) In N,N-dimethylformamide (10 ml) was dissolved 6-O-β-alanyl-N-acetylmuramyl-L-alanyl-D-isoglutamine (564 mg, 1 m mol), and under ice-cooling, N-ethylmorpholine (0.128 ml) and hydroquinone (1 mg) were added. Then, following addition of methacrylic acid N-hydroxysuccinimide ester (238 mg, 1.3 m mols), the mixture was reacted at 4° C. for 24 hours. The solvent was distilled off, the residue was treated with diethyl ether and the resultant powders were recovered by filtration and reprecipitated from ethanol-diethyl ether. By the above procedure there was obtained 555 mg of 2-[2-acetamido-2-deoxy-6-O-(methacryloyl-β-alanyl)-D-glucos-3-O-yl]-D-propionyl-L-alanyl-D-isoglutamine [hereinafter referred to as 6-O-(methacryloyl-β-alanyl)-N-acetylmuramyl-L-alanyl-D-isoglutamine.] m.p. 164° C. (decomp.); $[\alpha]_D^{24}+36.3°$ (after 3 min.)→+32.6° (after 25 hrs.) [c=0.405, water]; $Rf^3=0.29$.

Elemental analysis, for $C_{26}H_{41}O_{13}N_5 \cdot 3/2H_2O$; Calcd. C, 47.41; H, 6.73; N, 10.63; Found C, 47.34; H, 6.74; N, 10.64.

EXAMPLE 26

(1) 3-(2,3-Dimethoxy-5-methyl-1,4-benzoquinon-6-yl)propionic acid (38.1 mg, 0.15 m mol) and p-nitrophenol (23.0 mg, 0.165 m mol) were dissolved in acetonitrile (2 ml), and under ice cooling, N,N'-dicyclohexylcarbodiimide (34.0 mg, 0.165 m mol) was added. The mixture was stirred at 4° C. for 16 hours. The precipitate was removed and the solvent was distilled off under reduced pressure to recover 3-(2,3-dimethoxy-5-methyl-1,4-benzoquinon-6-yl)-propionic acid p-nitrophenyl ester.

(2) In N,N-dimethylformamide (1.2 ml) was dissolved 6-O-glycyl-N-acetylmuramyl-L-alanyl-D-isoglutamine (82.4 mg, 0.15 m mol) obtained in Example 1-(2), and under ice-cooling, N-ethylmorpholine (19.2 μl) was added. To this solution was added the 3-(2,3-dimethoxy-5-methyl-1,4-benzoquinon-6-yl)-propionic acid p-nitrophenyl ester obtained in (1) and the reaction was carried out at room temperature for 16 hours. The reaction product was purified in the same manner as Example 17-(2). By the above procedure there was obtained 79.0 mg of 2-{2-acetamido-2-deoxy-6-O-[3-(2,3-dimethoxy-5-methyl-1,4-benzoquinon-6-yl)-propionyl-glycyl]-D-glucos-3-O-yl}-D-propionyl-L-alanyl-D-isoglutamine. $[\alpha]_D^{30}+33.3°$ (c=0.5, ethanol); $Rf^2=0.62$; $Rf^3=0.29$.

Elemental analysis, for $C_{33}H_{47}O_{17}N_5 \cdot H_2O$; Calcd. C, 49.31; H, 6.15; N, 8.71; Found: C, 49.20; H, 6.27; N, 8.63.

EXAMPLE 27

In the same manner as Example 22, 10-(2,3-dimethoxy-5-methyl-1,4-benzoquinon-6-yl)-decanoic acid (33.8 mg, 0.1 m mol), p-nitrophenol (16.7 mg, 0.12 m mol) and N,N'-dicyclohexylcarbodiimide (24.7 mg, 0.12 m mol) were reacted in acetonitrile (2 ml) and the reaction product was treated. The active ester thus obtained and 2-(2-acetamido-2-deoxy-6-O-L-leucyl-D-glucos-3-O-yl)-D-propionyl-L-seryl-D-isoglutamine (62.1 mg, 0.1 m mol) obtained in Example 5-(6) were reacted in N,N-dimethylformamide (2 ml) and in the presence of N-ethylmorpholine (20 μl) at room temperature for 24 hours. The solvent was distilled off and the residue was purified as in Example 17-(2). By the above procedure there was obtained 48.4 mg of 2-{2-acetamido-2-deoxy-6-O-[10-(2,3-dimethoxy-5-methyl-1,4-benzoquinon-6-yl)-decanoyl-L-leucyl]-D-glucos-3-O-yl}-D-propionyl-L-seryl-D-isoglutamine. $[\alpha]_D^{23}+17.1°$ (after 3 min.)→+16.7° (after 25 hrs.) [c=0.5, 70% ethanol); $Rf^3=0.50$.

Elemental analysis, for $C_{44}H_{69}O_{18}N_5 \cdot 2H_2O$; Calcd. C, 53.27; H, 7.42; N, 7.06; Found C, 53.40; H, 7.09; N, 7.05.

EXAMPLE 28

In the same manner as Example 22, 3-(2,3-dimethoxy-5-methyl-1,4-benzoquinon-6-yl)-propionic acid (38.1 mg, 0.15 m mol), p-nitrophenol (22.9 mg, 0.165 m mol) and N,N'-dicyclohexylcarbodiimide (34 mg, 0.165 m mol) were reacted in acetonitrile (2 ml) and the reaction product was treated. The active ester thus obtained and 2-(2-acetamido-2-deoxy-6-O-L-prolyl-D-glucos-3-O-yl)-D-propionyl-L-alanyl-D-isoglutamine (88.5 mg, 0.15 m mol) obtained in Example 4-(2) were reacted in the presence of N-ethylmorpholine (30 μl) using N,N-dimethylformamide (2 ml) as the solvent at room temperature for 24 hours. The solvent was distilled off and the residue was purified as in Example 17-(2). By the above procedure there was obtained 63 mg of 2-{2-acetamido-2-deoxy-6-O-[3-(2,3-dimethoxy-5-methyl-1,4-benzoquinon-6-yl)-propionyl-L-prolyl]-D-glucos-3-O-yl}-D-propionyl-L-alanyl-D-isoglutamine. $[\alpha]_D^{23}+10.4°$ (after 3 min.)→+10.4° (after 25 hrs.) [c=0.5, 70% ethanol]; $Rf^3=0.41$.

Elemental analysis, for $C_{36}H_{51}O_{17}N_5 \cdot 3H_2O$; Calcd. C, 49.13; H, 6.53; N, 7.96; Found: C, 49.22; H, 5.98; N, 8.05.

EXAMPLE 29

In N,N-dimethylformamide (1 ml) was dissolved 6-O-ε-amino-n-caproyl-N-acetylmuramyl-L-alanyl-D-isoglutamine (75.7 mg, 125 μmols) obtained in Example 3-(2), and under ice-cooling, N-ethylmorpholine (16 μl)

was added. To this solution was added 10-(2,3-dimethoxy-5-methyl-1,4-benzoquinon-6-yl)-decanoic acid p-nitrophenyl ester (59.2 mg, 125 μmols) and the reaction was carried out at room temperature for 16 hours. The reaction product was purified as in Example 17-(2). By the above procedure there was obtained 94 mg of 2-{2-acetamido-2-deoxy-6-O-[10-(2,3-dimethoxy-5-methyl-1,4-benzoquinon-6-yl)-decanoyl-ε-amino-n-caproyl]-D-glucos-3-O-yl}-D-propionyl-L-alanyl-D-isoglutamine. $[\alpha]_D^{23}+28.6°$ (c=0.5, ethanol); $Rf^2=0.79$; $Rf^3=0.52$.

Elemental analysis, for $C_{44}H_{69}O_{17}N_5 \cdot H_2O$; Calcd. C, 55.15; H, 7.47; N, 7.31; Found C, 54.97; H, 7.24; N, 7.25.

EXAMPLE 30

In N,N-dimethylformamide (1 ml) was dissolved 2-(2-acetamido-2-deoxy-6-O-glycyl-D-glucos-3-O-yl)-D-propionyl-α-aminoisobutyroyl-D-isoglutamine (56.4 mg, 0.1 m mol) obtained in Example 7-(5), and under ice-cooling, N-ethylmorpholine (12.8 μl) was added. To this solution was added 10-(2,3-dimethoxy-5-methyl-1,4-benzoquinon-6-yl)-decanoic acid p-nitrophenyl ester (47.4 mg, 0.1 m mol). The mixture was stirred at room temperature for 16 hours and the reaction product was purified as in Example 17-(2). By the above procedure there was obtained 50.5 mg of 2-{2-acetamido-2-deoxy-6-O-[10-(2,3-dimethoxy-5-methyl-1,4-benzoquinon-6-yl)-decanoyl-glycyl]-D-glucos-3-O-yl}-D-propionyl-α-aminoisobutyroyl-D-isoglutamine. $[\alpha]_D^{23}+30.6°$ (c=0.5, ethanol); $Rf^2=0.79$; $Rf^3=0.61$.

Elemental analysis, for $C_{41}H_{63}O_{17}N_5 \cdot 3H_2O$; Calcd. C, 52.21; H, 7.37; N, 7.25; Found C, 52.14; H, 7.20; N, 7.34.

EXAMPLE 31

2-[2-Acetamido-6-O-(11-aminoundecanoyl)-2-deoxy-D-glucos-3-O-yl]-D-propionyl-L-alanyl-D-isoglutamine (101.4 mg, 0.15 m mol) obtained in Example 9-(4) was reacted with 3-(2,3-dimethoxy-5-methyl-1,4-benzoquinon-6-yl)-propionic acid p-nitrophenyl ester (56.3 mg, 0.15 m mol) in N,N-dimethylformamide (1.5 ml) and in the presence of N-ethylmorpholine (0.03 ml) at room temperature for 60 hours. The reaction product was then purified as in Example 17-(2). By the above procedure there was obtained 70 mg of 2-{2-acetamido-2-deoxy-6-O-[3-(2,3-dimethoxy-5-methyl-1,4-benzoquinon-6-yl)-propionyl-11-aminoundecanoyl]-D-glucos-3-O-yl}-D-propionyl-L-alanyl-D-isoglutamine. $[\alpha]_D^{23}+25.1°$ (after 3 min.)→+25.4° (after 25 hrs.) [c=0.5, 70% ethanol); $Rf^3=0.43$.

Elemental analysis, for $C_{42}H_{65}O_{17}N_5 \cdot H_2O$; Calcd. C, 54.24; H, 7.26; N, 7.53; Found: C, 54.42; H, 7.38; N, 7.50.

EXAMPLE 32

2-{2-Acetamido-2-deoxy-6-O-[10-(2,3-dimethoxy-5-methyl-1,4-benzoquinon-6-yl)-decanoyl-glycyl)-D-glucos-3-O-yl}-D-propionyl-L-valyl-D-isoglutamine was produced in a manner similar to Example 28. $[\alpha]_D^{22}+26.0°$ (c=0.5, 85% ethanol); $Rf^3=0.62$;

Elemental analysis, for $C_{42}H_{65}O_{17}N_5 \cdot 2H_2O$; Calcd. C, 53.20; H, 7.34; N, 7.39; Found C, 53.36; H, 7.21; N, 7.54.

EXAMPLES 33 TO 44

The following compounds were produced by the reaction and purification procedures similar to those set forth in the preceding examples.

EXAMPLE 33

2-{2-Acetamido-2-deoxy-6-O-[10-(2,3-dimethoxy-5-methyl-1,4-benzoquinon-6-yl)-decanoyl-11-aminoundecanoyl]-D-glucos-3-O-yl}-D-propionyl-L-alanyl-D-isoglutamine. $[\alpha]_D^{20}+26.7°$ (c=0.5, ethanol); $Rf^3=0.51$.

Elemental analysis, for $C_{49}H_{79}O_{17}N_5$; Calcd. C, 56.74; H, 7.97; N, 6.75; Found C, 56.78; H, 7.90; N, 6.78.

EXAMPLE 34

2-{2-Acetamido-2-deoxy-6-O-[10-(2,3-dimethoxy-5-methyl-1,4-benzoquinon-6-yl)-decanoyl-L-leucyl]-D-glucos-3-O-yl}-D-propionyl-α-aminoisobutyroyl-D-isoglutamine. $[\alpha]_D^{20}+23.4°$ (c=0.5, ethanol), $Rf^3=0.58$.

Elemental analysis, for $C_{45}H_{71}O_{17}N_5 \cdot H_2O$; Calcd. C, 55.59; H, 7.57; N, 7.21; Found C, 55.60; H, 7.49; N, 7.14.

EXAMPLE 35

2-{2-Acetamido-2-deoxy-6-O-[3-(2,3-dimethoxy-5-methyl-1,4-benzoquinon-6-yl)-propionyl-L-leucyl]-D-glucos-3-O-yl}-D-propionyl-α-aminoisobutyroyl-D-isoglutamine $[\alpha]_D^{20}+26.2°$ (c=0.5, ethanol), $Rf^3=0.48$.

Elemental analysis, for $C_{38}H_{57}O_{17}N_5 \cdot H_2O$; Calcd. C, 51.17; H, 6.89; N, 7.85; Found C, 51.22; H, 6.52; N, 7.76.

EXAMPLE 36

2-{2-Acetamido-2-deoxy-6-O-[6-(2,3,5-trimethyl-1,4-benzoquinon-6-O-yl)-hexanoyl-L-leucyl]-D-glucos-3-O-yl}-D-propionyl-α-aminoisobutyroyl-D-isoglutamine. $[\alpha]_D^{22}+26.6°$ (c=0.5, ethanol), $Rf^3=0.48$.

Elemental analysis, for $C_{41}H_{63}O_{15}N_5 \cdot H_2O$; Calcd. C, 55.70; H, 7.41; N, 7.92; Found: C, 55.65; H, 7.58; N, 8.06.

EXAMPLE 37

2-{2-Acetamido-2-deoxy-6-O-[9-(2-methyl-1,4-naphthoquinon-3-yl)-nonanoyl-L-leucyl]-D-glucos-3-O-yl}-D-propionyl-α-aminoisobutyroyl-D-isoglutamine. $[\alpha]_D^{22}+20.2°$ (c=0.5, ethanol), $Rf^3=0.54$.

Elemental analysis, for $C_{46}H_{67}O_{15}N_5 \cdot 2H_2O$; Calcd. C, 57.19; H, 7.41; N, 7.25; Found C, 57.11; H, 7.21; N, 7.26.

EXAMPLE 38

2-{2-Acetamido-2-deoxy-6-O-[10-(2,3-dimethoxy-5-methyl-1,4-benzoquinon-6-yl)-decanoyl-D-leucyl]-D-glucos-3-O-yl}-D-propionyl-α-aminoisobutyroyl-D-isoglutamine. $[\alpha]_D^{20}+37.6°$ (c=0.5, ethanol), $Rf^3=0.56$.

Elemental analysis, for $C_{45}H_{71}O_{17}N_5 \cdot 3/2H_2O$; Calcd. C, 55.09; H, 7.60; N, 7.14; Found C, 54.91; H, 7.23; N, 7.29.

EXAMPLE 39

2-{2-Acetamido-2-deoxy-6-O-[3-(2,3-dimethoxy-5-methyl-1,4-benzoquinon-6-yl)-propionyl-D-leucyl]-D-glucos-3-O-yl}-D-propionyl-α-aminoisobutyroyl-D-isoglutamine. $[\alpha]_D^{20}+39.4°$ (c=0.5, ethanol), $Rf^3=0.44$.

Elemental analysis, for $C_{38}H_{57}O_{17}N_5 \cdot 2H_2O$; Calcd. C, 51.17; H, 6.89, N, 7.85; Found C, 51.18; H, 6.62; N, 7.73.

EXAMPLE 40

2-{2-Acetamido-2-deoxy-6-O-[10-(2,3-dimethoxy-5-methyl-1,4-benzoquinon-6-yl)-decanoyl-11-aminodecanoyl]-D-glucos-3-O-yl}-D-propionyl-α- aminoisobutyroyl-D-isoglutamine. $[\alpha]_D^{20}+28.5°$ (c=0.5, ethanol), Rf$^3$=0.62.

Elemental analysis, for C$_{50}$H$_{81}$O$_{17}$N$_5$.3/2H$_2$O; Calcd. C, 57.12; H, 8.05; N, 6.66; Found C, 57.08; H, 8.10; N, 6.67.

EXAMPLE 41

2-{2-Acetamido-2-deoxy-6-O-[3-(2,3-dimethoxy-5-methyl-1,4-benzoquinon-6-yl)-propionyl-11-aminoundecanoyl]-D-glucos-3-O-yl}-D-propionyl-α-aminoisobutyroyl-D-isoglutamine. $[\alpha]_D^{20}+32.0°$ (c=0.5, ethanol), Rf$^3$=0.49.

Elemental analysis, for C$_{43}$H$_{67}$O$_{17}$N$_5$.H$_2$O; Calcd. C, 54.70; H, 7.37; N, 7.42; Found C, 54.89; H, 7.42; N, 7.46.

EXAMPLE 42

2-{2-Acetamido-2-deoxy-6-O-[10-(2,3-dimethoxy-5-methyl-1,4-benzoquinon-6-yl)-decanoyl-glycyl]-D-glucos-3-O-yl}-D-propionyl-α-aminoisobutyroyl-D-isoglutamine. $[\alpha]_D^{22}+30.2°$ (c=0.5, ethanol), Rf$^3$=0.52.

Elemental analysis, for C$_{42}$H$_{65}$O$_{17}$N$_5$.3H$_2$O; Calcd. C, 52.21; H, 7.37; N, 7.25; Found C, 52.14; H, 7.20; N, 7.34.

EXAMPLE 43

2-{2-Acetamido-2-deoxy-6-O-[10-(2,3-dimethoxy-5-methyl-1,4-benzoquinon-6-yl)-decanoyl-L-leucyl]-D-glucos-3-O-yl}-D-propionyl-L-valyl-D-isoglutamine. $[\alpha]_D^{22}+19.4°$ (c=0.5, ethanol); Rf$^3$=0.74

Elemental analysis, for C$_{46}$H$_{73}$O$_{17}$N$_5$.3/2H$_2$O; Calcd. C, 55.52; H, 7.70; N, 7.04; Found C, 55.56; H, 7.43; N, 6.98.

EXAMPLE 44

2-{2-Acetamido-2-deoxy-6-O-[9-(2-methyl-1,4-naphthoquinon-3-yl)-nonanoyl-L-leucyl]-D-glucos-3-O-yl}-D-propionyl-L-valyl-D-isoglutamine. $[\alpha]_D^{22}+12.6°$ (c=0.5, 90% ethanol); Rf$^3$=0.62.

Elemental analysis, for C$_{47}$H$_{69}$O$_{15}$N$_5$.3H$_2$O; Calcd. C, 56.55; H, 7.57; N, 7.02; Found C, 56.32; H, 7.12; N, 6.92.

EXAMPLE 45

6-O-(Methacryloyl-β-alanyl)-N-acetylmuramyl-L-alanyl-D-isoglutamine (530 mg, 0.84 m mol) obtained in Example 25-(2) was dissolved in N,N-dimethylformamide (2 ml) and, with α,α'-azobisisobutyronitrile (2.7 mg, 0.016 m mol) as a catalyst, the polymerization reaction was conducted at 60° C. in an atmosphere of nitrogen gas for 15 hours. The reaction mixture was poured in methanol (50 ml), whereupon an oil separated. The methanol layer was taken by decanting, the methanol was distilled off under reduced pressure and the residue was dissolved in N,N-dimethylformamide. Chloroform was added to the solution and the precipitate was recovered by filtration and reprecipitated from methanol-chloroform. By the above procedure there was obtained 125 mg of a homopolymer of 6-O-(methacryloyl-β-alanyl)-N-acetylmuramyl-L-alanyl-D-isoglutamine. The polymer had a molecular weight of about 2,000 as determined by vapor pressure osmometry, m.p. 154°–155° C.; $[\alpha]_D^{24}+35.5°$ (after 3 min.)→+34.8° (after 25 hrs.) [c=0.29, water]; Rf$^2$=0.00, Rf$^3$=0.00.

Elemental analysis, for (C$_{26}$H$_{41}$O$_{13}$N$_5$.3H$_2$O)$_n$; Calcd. C, 45.54; H, 6.91; N, 10.21; Found C, 45.47; H, 6.25; N, 10.39.

The oil mentioned above, on the other hand, was dissolved in N,N-dimethylformamide and, after addition of methanol, the solvent was removed by decanting and the residue was solidified with diethyl ether to obtain 145 mg of white powders. A 15 mg portion of the powdery product was put on a column of Bio-Gel P-200 (0.9×58 cm) and developed with 0.01 N aqueous sodium chloride solution. The effluent from the column was scanned by means of a differential refractometer and the fractions giving a first peak were collected. The solvent was distilled off, the residue was dissolved in water and the solution was dialyzed using cellophane tube against distilled water at room temperature for 24 hours, whereby the sodium chloride was removed. The dialysate was lyophilized to recover 8 mg of a homopolymer of 6-O-(methacryloyl-β-alanyl)-N-acetylmuramyl-L-alanyl-D-isoglutamine. This polymer had a molecular weight of about 50,000 as determined by gel-permeation chromatography with albumin, ovalbumin, etc. as standards. m.p. ≦260° C.; $[\alpha]_D^{24}+33.4°$ (after 3 min.)→+31.2° (after 25 hrs.) [c=0.4, water]; Rf$^2$=0.00, Rf$^3$=0.00

Elemental analysis, for (C$_{26}$H$_{41}$O$_{13}$N$_{15}$.½H$_2$O)$_n$; Calcd. C, 48.74; H, 6.61; N, 10.93; Found C, 48.64; H, 7.12; N, 10.07.

EXAMPLE 46

6-O-(methacryloyl-β-alanyl)-N-acetylmuramyl-L-alanyl-D-isoglutamine (530 mg, 0.84 m mol) and N-vinyl-2-pyrrolidone (93.4 mg, 0.84 m mol) were dissolved in N,N-dimethylformamide (4 ml) and, with α,α'-azobisisobutyronitrile (5.4 mg, 0.032 m mol) as a catalyst, the copolymerization reaction was conducted at 60° C. in an atmosphere of nitrogen gas for 15 hours. The reaction mixture was poured in diethyl ether (150 ml) and the resultant precipitate was collected by filtration. The powders thus obtained were reprecipitated from methanol-chloroform and, then, from N,N-dimethylformamide-chloroform to obtain 461 mg of a copolymer of 6-O-(Methacryloyl-β-alanyl)-N-acetylmuramyl-L-alanyl-D-isoglutamine with N-vinyl-2-pyrrolidone.

This copolymer had a molecular weight of about 1,500 as determined by vapor pressure osmometry. m.p. 169°–171° C. (decomp.); $[\alpha]_D^{25}+32.6°$ (after 3 min.)→+28.8° (after 25 hrs.) [c=0.5, water]; Rf$^2$=0.00, Rf$^3$=0.00.

Elemental analysis, for (C$_{26}$H$_{41}$O$_{13}$N$_5$.3H$_2$O)$_{3n}$(C$_6$H$_9$OH)$_{2n}$; Calcd. C, 47.43; found C, 47.22.

EXAMPLE 47

6-O-(methacryloyl-β-alanyl)-N-acetylmuramyl-L-alanyl-D-isoglutamine (530 mg, 0.84 m mol) and stearyl vinyl ether (249.1 mg, 0.84 m mol) were dissolved in N,N-dimethylformamide (4 ml) and, with α,α'-azobisisobutyronitrile (5.4 mg, 0.032 m mol) as a catalyst, the copolymerization reaction was carried out in the same manner as Example 46. The reaction mixture was poured in diethyl ether (150 ml) and the precipitate was collected by filtration. The powders thus obtained were reprecipitated from methanol-chloroform twice and, then, from N,N-dimethylformamide-chloroform once. By the above procedure there was obtained 214 mg of a copolymer of 6-O-(methacryloyl-β-alanyl)-N-acetylmuramyl-L-alanyl-D-isoglutamine with stearyl vinyl ether.

This copolymer had a molecular weight of about 3,000 as determined by vapor pressure osmometry. m.p.

172°–175° C. (decomp.); $[\alpha]_D^{25}$ +30.4° (after 3 min.)→+27.4° (after 25 hrs.); [c=0.5, water]; $Rf^2$=0.00, $Rf^3$=0.00.

Elementary analysis, for $(C_{26}H_{41}O_{13}N_5\cdot 3H_2O)_{3n}(C_{20}H_{40}O)_n$; Calcd. N, 8.93; found N, 8.90.

EXAMPLE 48

6-O-(methacryloyl-β-alanyl)-N-acetylmuramyl-L-alanyl-D-isoglutamine (265 mg, 0.42 m mol) and tridecyl methacrylate (113 mg, 0.42 m mol) were copolymerized in N,N-dimethylformamide (2 ml) with α,α'-azobisisobutyronitrile (2.7 mg, 0.016 m mol) as the catalyst in the same manner as Example 46. The reaction mixture was poured in diethyl ether (75 ml) and the precipitate was recovered by filtration and reprecipitated from methanol-chloroform. By the above procedure there was obtained 98 mg of a copolymer of 6-O-(methacryloyl-β-alanyl)-N-acetylmuramyl-L-alanyl-D-isoglutamine with tridecyl methacrylate. Mol. wt. ca. 1,500 (vapor pressure osmometry); m.p. 158° C. (decomp.); $[\alpha]_D^{23}$+25.1° (after 3 min.)→+24.2° (after 25 hrs.) [c=0.5, water]; $Rf^2$=0.00, $Rf^3$=0.00.

Elemental analysis, for $(C_{26}H_{41}O_{13}N_5\cdot 3H_2O)_{7n}(C_{17}H_{32}O_2)_{3n}$; Calcd. N, 8.61; found N, 8.90.

EXAMPLE 49

(1) Acrylic acid (stabilized with ca. 0.02% of a quinone compound) (72.1 mg, 1 m mol) and p-nitrophenol (153 mg, 1.1 m mols) were dissolved in acetonitrile (3 ml), and under ice-cooling, N,N'-dicyclohexylcarbodiimide (227 mg, 1.1 m mols) was added. The mixture was stirred at 4° C. for 16 hours, at the end of which time the solvent was distilled off under reduced pressure at low temperature (<5° C.) under exclusion of light. The residue was dissolved in N,N-dimethylformamide (10 ml), together with 6-O-β-alanyl-N-acetylmuramyl-L-alanyl-D-isoglutamine (563.5 mg, 1 m mol). The reaction was carried out in the presence of N-ethylmorpholine (0.128 ml, 1 m mol) and hydroquinone (1 mg) at 4° C. for 72 hours. Then, as in Example 25-(2), the reaction product was purified to obtain 266 mg of 2-[2-acetamido-6-O-(acryloyl-β-alanyl)-2-deoxy-D-glucos-3-O-yl]-D-propionyl-L-alanyl-D-isoglutamine. $[\alpha]_D^{22}$ +31.8° (after 3 min.)→+29.8° (after 25 hrs.) [c=0.5, water], $Rf^2$=0.57.

Elemental analysis, for $C_{28}H_{45}O_{13}N_5\cdot 2H_2O$; Calcd. C, 48.33; H, 7.10; N, 10.07; Found C, 47.59; H, 6.51; N, 10.69.

(2) 2-[2-acetamido-6-O-(acryloyl-β-alanyl)-2-deoxy-D-glucos-3-O-yl]-D-propionyl-L-alanyl-D-isoglutamine (185.3 mg, 0.3 m mol) was dissolved in N,N-dimethylformamide (0.5 ml) and addition of α,α'-azobisisobutyronitrile (0.98 mg) as the catalyst followed. The solution was stirred in an atmosphere of nitrogen gas at 60° C. for 16 hours. To the reaction mixture was added diethyl ether and the resultant precipitate was recovered by filtration. The resultant powders were reprecipitated five times from methanol-chloroform. By the above procedure there was obtained 41.6 mg of a homopolymer of 2-[2-acetamido-6-O-(acryloyl-β-alanyl)-2-deoxy-D-glucos-3-O-yl]-D-propionyl-L-alanyl-D-isoglutamine. Mol. wt. ca. 1,500 (vapor osmometry); $[\alpha]_D^{21}$ +25.0 (after 3 min.)→+22.6° (after 25 hrs.) [c=0.5, water]; $Rf^2$=0.00, $Rf^3$=0.00.

Elemental analysis, for $(C_{28}H_{45}O_{13}N_5\cdot 2.5H_2O)_n$; Calcd. C, 47.72; H, 7.15; N, 9.94; Found C, 47.31; H, 6.36; N, 10.49.

EXAMPLE 50

(1) 2-(2-Acetamido-2-deoxy-6-O-L-leucyl-D-glucos-3-O-yl)-D-propionyl-L-seryl-D-isoglutamine (186 mg, 0.3 m mol) obtained in Example 5-(6) and hydroquinone (0.3 mg) were dissolved in N,N-dimethylformamide (2 ml) and, after the addition of N-ethylmorpholine (0.051 ml, 0.4 m mol) and methacrylic acid N-hydroxysuccinimide ester (73 mg, 0.4 m mol) were added under ice-cooling, the mixture was stirred at 4° C. for 20 hours. The precipitate resulting from addition of diethyl ether, was recovered by filtration. By the above procedure there was obtained 193 mg of 2-[2-acetamido-2-deoxy-6-O-(methacryloyl-L-leucyl)-D-glucos-3-O-yl]-D-propionyl-L-alanyl-D-isoglutamine [hereinafter referred to as 6-O-(methacryloyl-L-leucyl)-N-acetylmuramyl-L-seryl-D-isoglutamine). m.p. 136° C. (decomp.); $[\alpha]_D^{22}$ +15.0° (after 3 min.)→+12.4° (after 25 hrs.) (c=0.5, water); $Rf^3$=0.25

Elemental analysis, for $C_{29}H_{47}O_{14}N_5\cdot H_2O$; Calcd. C, 49.21; H, 6.98; N, 9.90; Found C, 49.12; H, 7.03; N, 10.15.

(2) 6-O-(methacryloyl-L-leucyl)-N-acetylmuramyl-L-seryl-D-isoglutamine (170 mg, 0.24 m mol) was dissolved in N,N-dimethylformamide (0.25 ml), followed by addition of α,α'-azobisisobutyronitrile (0.9 mg, 0.005 m mol) as the catalyst. In an atmosphere of $N_2$, the reaction was conducted at 60° C. for 15 hours, after which diethyl ether (15 ml) was added to the reaction mixture. The resultant precipitate was recovered by filtration and washed with hot methanol to obtain 69 mg of a homopolymer of 6-O-(methacryloyl-L-leucyl)-N-acetylmuramyl-L-seryl-D-isoglutamine. Mol. wt. ca. 2,500 (vapor pressure osmometry); m.p. 185° C. (decomp.); $[\alpha]_D^{22}$ +13.2° (after 3 min.)→+10.5° (after 25 hrs.) [c=0.5, water]; $Rf^2$=0.00, $Rf^3$=0.00.

Elemental analysis, for $C_{29}H_{47}O_{14}N_5\cdot H_2O$; Calcd. C, 49.21; H, 6.98; N, 9.90; Found C, 49.03; H, 6.94; N, 9.48.

EXAMPLE 51

(1) 2-(2-Acetamido-6-O-(ε-amino-n-caproyl)-2-deoxy-D-glucos-3-O-yl]-D-propionyl-α-aminoisobutyroyl-D-isoglutamine (155 mg, 0.25 m mol) obtained in Example 8-(2) was dissolved in N,N-dimethylformamide (2 ml) and, under ice-cooling, N-ethylmorpholine (38.4 μl), hydroquinone (3 mg) and methacrylic acid N-hydroxysuccinimide ester (55 mg, 0.3 m mol) were added. After being stirred at 4° C. for 24 hours, the mixture was concentrated and the concentrate was applied onto a silica gel column, elution being then carried out with ethyl acetate-pyridine-acetic acid-water (30:10:3:5). The fractions rich in the dominant product were pooled, the solvent was distilled off, the residue was applied onto a Sephadex LH-20 column and elution was carried out with ethanol-0.1 N acetic acid (3:2). By the above procedure there was obtained 94.4 mg of 2-[2-acetamido-2-deoxy-6-O-(methacryloyl-ε-amino-n-caproyl)-D-glucos-3-O-yl]-D-propionyl-α-aminoisobutyroyl-D-isoglutamine [hereinafter, 6-O-(methacryloyl-ε-amino-n-capropyl)-N-acetylmuramyl-α-aminoisobutyroyl-D-isoglutamine.] $[\alpha]_D^{23}$ +43.7° (c=1.0, 70% ethanol); $Rf^1$=0.50.

Elemental analysis, for $C_{30}H_{49}O_{13}N_5\cdot H_2O$; Calcd. C, 51.05; H, 7.28; N, 9.92; Found C, 50.95; H, 7.45; N, 9.77.

(2) 6-O-(methacryloyl-ε-amino-n-caproyl)-N-acetylmuramyl-α-aminoisobutyroyl-D-isoglutamine (425 mg, 0.62 m mol) was dissolved in N,N-dimethylformamide (1 ml) and, with the addition of α,α'-azobisisobutyronitrile (5.1 mg, 0.031 m mol) as the catalyst, the solution was stirred in an atmosphere of $N_2$ at 60° C. for 16 hours. The solvent was distilled off, the residue was dissolved in N,N-dimethylformamide (0.4 ml), chloroform (7.5 ml) was added and the precipitate was recovered by filtration. It was redissolved in N,N-dimethylformamide (0.4 ml) and reprecipitated by the addition of methanol (7.5 ml). By the above procedure there was obtained 105 mg of a homopolymer of 6-O-(methacryloyl-ε-amino-n-caproyl)-N-acetylmuramyl-α-aminoisobutyroyl-D-isoglutamine. Mol. wt. ca. 2,500 (vapor pressure osmometry); m.p. 174° C. (sinter); $[\alpha]_D^{23}$ +33.6° (after 3 min.)→+31.6° (after 24 hrs.) [c=0.5, water]; $Rf^2$=0.00, $Rf^3$=0.00.

Elemental analysis, for $(C_{30}H_{49}O_{13}N_5 \cdot 4H_2O)_n$; Calcd. C, 47.42; H, 7.56; N, 9.22; Found C, 47.32; H, 6.87; N, 8.81

(3) In water (5 ml) was dissolved 70 mg of the homopolymer of 6-O-(methacryloyl-ε-amino-n-caproyl)-N-acetylmuramyl-α-aminoisobutyroyl-D-isoglutamine and the solution was adjusted to pH 7 by the dropwise addition of 0.5 N-sodium hydroxide. It was lyophilized twice. By the above procedure there was obtained the Na salt of the 6-O-(methacryloyl-ε-amino-n-caproyl)-N-acetylmuramyl-α-aminoisobutyroyl-D-isoglutamine homopolymer in quantitative yield.

Elemental analysis, for $(C_{30}H_{48}O_{13}N_5Na \cdot 3/2H_2O)_n$; Calcd. C, 48.91; H, 6.98; N, 9.51; Found C, 49.22; H, 6.59; N, 9.01

EXAMPLE 52

(1) In the same manner as Example 25-(2), 2-[2-acetamido-6-O-(11-aminoundecanoyl)-2-deoxy-D-glucos-3-O-yl]-D-propionyl-L-alanyl-D-isoglutamine (203 mg, 0.3 m mol) and methacrylic acid N-hydroxysuccinimide ester (69 mg, 0.38 m mol) were reacted in N,N-dimethylformamide (1 ml) and in the presence of N-ethylmorpholine, and the reaction product was worked up. By the above procedure there was obtained 119 mg of 2-[2-acetamido-6-O-(methacryloyl-11-aminoundecanoyl)-2-deoxy-D-glucos-3-O-yl]-D-propionyl-L-alanyl-D-isoglutamine. m.p. 117° C.; $[\alpha]_D^{21}$ +35.0° (c=0.5, N,N-dimethylformamide); $Rf^3$=0.31

Elemental analysis, for $C_{34}H_{57}O_{13}N_5 \cdot \frac{1}{2}H_2O$; Calcd. C, 54.26; H, 7.77; N, 9.30; Found C, 54.12; H, 7.99; N, 9.32.

(2) In N,N-dimethylformamide (0.2 ml) were dissolved 2-[2-acetamido-6-O-(methacryloyl-11-aminoundecanoyl)-2-deoxy-D-glucos-3-O-yl]-D-propionyl-L-alanyl-D-isoglutamine (170 mg, 0.23 m mol), and α,α'-azobisisobutyronitrile (0.9 mg, 0.005 m mol). The solution was stirred in an atmosphere of $N_2$ at 60° C. for 15 hours. Diethyl ether (20 ml) was added to the reaction mixture. The resultant precipitate was recovered by filtration and then boiled in ethanol (15 ml). Insoluble oily material was, after cooling, pulverized and collected by filtration. By the above procedure there was obtained 69 mg of a homopolymer of 2-[2-acetamido-6-O-(methacryloyl-11-aminoundecanoyl)-2-deoxy-D-glucos-3-O-yl]-D-propionyl-L-alanyl-D-isoglutamine. Mol. wt. ca. 4,000 (vapor pressure osmometry); m.p. 172° C. (decomp.); $[\alpha]_D^{21}$ +32.1° (c=0.5, N,N-dimethylformamide); $Rf^2$=0.00, $Rf^3$=0.00.

Elemental analysis, for $(C_{34}H_{57}O_{13}N_5 \cdot 2H_2O)_n$; Calcd. C, 52.38; H, 7.89; N, 8.99; Found C, 52.57; H, 7.62; N, 8.33.

EXAMPLE 53

Eight (8) mg of 6-O-β-alanyl-N-acetylmuramyl-L-alanyl-D-isoglutamine was dissolved in 3.5 ml of phosphate buffered saline and sterilized in the usual manner. The sterilized solution was added dropwise, with vigorous stirring, to 0.5 ml of a sterile mixture of hydrogenated vegetable triglyceride (Migryol 812) and mannitol monooleate (17:3) to prepare a water-in-oil emulsion. This product, in 0.5 ml aliquot per adult human, is useful for parenteral administration.

EXAMPLE 54

Two (2) mg. of 2-{2-acetamido-2-deoxy-6-O-[10-(2,3-dimethoxy-5-methyl-1,4-benzoquinon-6-yl)-decanoyl-L-leucyl]-D-glucos-3-O -yl}-D-propionyl-L-seryl-D-isoglutamine was treated with 10 μg of squalene and, then, vigorously homogenized with 1 ml of phosphate-buffered saline containing 0.2% of Tween 80 or 1 ml of physiological saline containing 0.2% of Tween 80 to prepare an oil-in-water emulsion. This product, in doses of 0.5 ml per adult human, is useful for parenteral administration.

EXAMPLE 55

In a sufficient amount of distilled water was dissolved 500 mg of the 6-O-(methacryloyl-β-alanyl)-N-acetylmuramyl-L-alanyl-D-isoglutamine homopolymer (mol. wt. ca. 2,000) obtained in Example 45, together with 5 g of mannitol, to make a total of 1,000 ml. The solution was filtered bacterial-free, distributed in 2 ml portions into vials and lyophilized. The contents of the vials are diluted with distilled water prior to use for injections.

What is claimed is:

1. A compound of the following formula or a physiologically acceptable salt thereof:

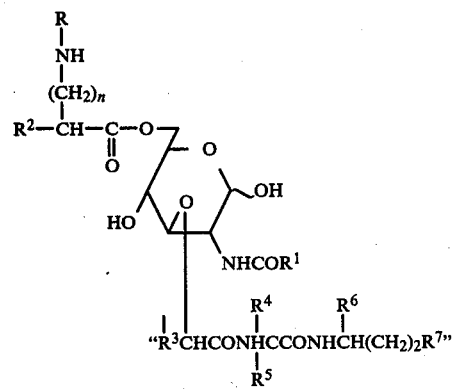

wherein
n is zero or an integer of 1 to 9;
$R^1$ is lower alkyl;
$R^2$ is hydrogen or lower alkyl when n is zero, and hydrogen or amino when n is an integer of 1 to 9;
$R^3$ is lower alkyl;
$R^4$ and $R^5$, independently of each other, are hydrogen, lower alkyl or hydroxymethyl;
$R^6$ and $R^7$, independently of each other, are a carboxyl group which may be amidated;
R is hydrogen or a group of the formula R'CO— wherein R' is an acyclic hydrocarbon group which may be substituted by a cyclic hydrocarbon group at its ω-position or a group of the formula

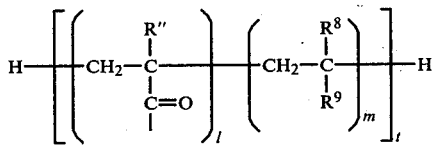

wherein
l is an integer of 1 to 9;
m is zero or an integer of 1 to 9;
t is an integer of 2 to 100;
R" is hydrogen or lower alkyl;
$R^8$ is hydrogen or lower alkyl;
$R^9$ is lower alkyl, a carboxyl group which may be esterified, a hydroxyl group which may be etherified or a pyrrolidino group which may be substituted by oxo, halogen, lower alkyl, nitro, amino or cyano;
l and m are variable within the said respective ranges and $R^8$ and $R^9$ are variable within the said definition, in the respective repeating units.

2. A compound according to claim 1, wherein $R^6$ is carbamoyl and $R^7$ is a free carboxyl group.

3. A compound according to claim 1 or 2, wherein $R^4$ is hydrogen and $R^5$ is isopropyl.

4. A compound according to claim 1 or 2, wherein $R^4$ is hydrogen and $R^5$ is hydroxylmethyl.

5. A compound according to claim 1, wherein R is hydrogen.

6. A compound according to claim 1, wherein R is the group of the formula R'CO—.

7. A compound according to claim 6, wherein R' is an acyclic hydrocarbon group containing up to 41 carbon atoms, the ω-position of which may be substituted by a six-membered unsaturated cyclic hydrocarbon group which may have 1 to 3 substituents selected from lower alkyl, lower alkoxy and oxo on its ring.

8. A compound according to claim 7, wherein the acyclic hydrocarbon group is one containing 2 to 9 carbon atoms substituted by the six-membered unsaturated cyclic hydrocarbon group at its ω-position.

9. A compound according to claim 8, wherein the six-membered unsaturated cyclic hydrocarbon group is 2,3-dimethoxy-5-methyl-1,4-benzoquinon-6-yl.

10. A compound according to claim 6, wherein the group of the formula R'CO— is 10-(2,3-dimethoxy-5-methyl-1,4-benzoquinon-6-yl)-decanoyl.

11. A compound according to claim 1, wherein R is the group of the formula

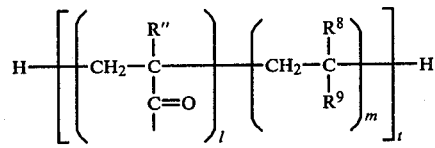

12. A compound according to claim 1, said compound being 2-{2-acetamido-2-deoxy-6-O-[10-(2,3-dimethoxy-5-methyl-1,4-benzoquinon-6-yl)-decanoyl-glycyl]-D-glucos-3-O-yl}-D-propionyl-L-valyl-D-isoglutamine.

13. A compound according to claim 1, said compound being 2-{2-acetamido-2-deoxy-6-O-[10-(2,3-dimethoxy-5-methyl-1,4-benzoquinon-6-yl)-decanoyl-L-leucyl]-D-glucos-3-O-yl}-D-propionyl-L-valyl-D-isoglutamine.

14. A compound according to claim 1, said compound being 2-{2-acetamido-2-deoxy-6-O-[10-(2,3-dimethoxy-5-methyl-1,4-benzoquinon-6-yl)-decanoyl-L-leucyl]-D-glucos-3-O-yl}-D-propionyl-L-seryl-D-isoglutamine.

* * * * *